US012569218B2

(12) United States Patent
Artunduaga

(10) Patent No.: US 12,569,218 B2
(45) Date of Patent: Mar. 10, 2026

(54) SYSTEMS, DEVICES, AND METHODS FOR PERFORMING ACTIVE AUSCULTATION AND DETECTING ACOUSTIC SIGNALS AND/OR SONIC ENERGY MEASUREMENTS

(71) Applicant: SAMAY, INC., Mountain View, CA (US)

(72) Inventor: Maria Artunduaga, Mountain View, CA (US)

(73) Assignee: SAMAY, INC., Mountain View, CA (US)

( * ) Notice: Subject to any disclaimer, the term of this patent is extended or adjusted under 35 U.S.C. 154(b) by 175 days.

(21) Appl. No.: 18/579,345

(22) PCT Filed: Jul. 18, 2022

(86) PCT No.: PCT/US2022/037518
§ 371 (c)(1),
(2) Date: Jan. 13, 2024

(87) PCT Pub. No.: WO2023/003833
PCT Pub. Date: Jan. 26, 2023

(65) Prior Publication Data
US 2024/0315661 A1 Sep. 26, 2024

Related U.S. Application Data

(60) Provisional application No. 63/223,506, filed on Jul. 19, 2021.

(51) Int. Cl.
A61B 7/04 (2006.01)
A61B 5/00 (2006.01)
(Continued)

(52) U.S. Cl.
CPC .............. *A61B 7/04* (2013.01); *A61B 5/0048* (2013.01); *A61B 5/02055* (2013.01); *A61B 5/08* (2013.01);
(Continued)

(58) Field of Classification Search
CPC ................................ A81B 7/04; A61B 5/6804
(Continued)

(56) References Cited

U.S. PATENT DOCUMENTS 4,598,417 A * 7/1986 Deno ........................ A61B 7/04
381/95
5,539,831 A 7/1996 Harley
(Continued)

OTHER PUBLICATIONS

Respira Labs, Inc.; International Application No. PCT/US2022/037518 filed Jul. 18, 2022; International Search Report and Written Opinion; ISA/US; Oct. 14, 2022; 11 pp.

*Primary Examiner* — William J Deane, Jr.
(74) *Attorney, Agent, or Firm* — Resonance IP Law, PC

(57) ABSTRACT
A device for performing active auscultation comprising: a main body; a body attachment structure; and one or more wings; wherein said main body comprises memory, battery, IMU, transceiver, and DSP; wherein said one or more wings comprise a microphone wing and a speaker wing; wherein said microphone wing comprises one or more microphones; wherein said speaker wing comprises a speaker; wherein said one or more wings comprise a temperature sensor; wherein said main body is configured to engage said body attachment structure; wherein said body attachment structured is configured to engage, on a first side said main body, and on a second side an animal body.

22 Claims, 19 Drawing Sheets

400

203, 301, 302, 303, or 304

(51) Int. Cl.

| | |
|---|---|
| *A61B 5/0205* | (2006.01) |
| *A61B 5/08* | (2006.01) |
| *A61B 7/00* | (2006.01) |

(52) U.S. Cl.
CPC .......... *A61B 5/6823* (2013.01); *A61B 5/7203* (2013.01); *A61B 5/725* (2013.01); *A61B 5/7271* (2013.01); *A61B 5/742* (2013.01); *A61B 7/003* (2013.01); *A61B 5/6804* (2013.01); *A61B 5/6831* (2013.01); *A61B 5/6832* (2013.01); *A61B 2560/0223* (2013.01); *A61B 2560/0406* (2013.01); *A61B 2560/045* (2013.01); *A61B 2560/0462* (2013.01); *A61B 2562/0204* (2013.01); *A61B 2562/0219* (2013.01); *A61B 2562/0271* (2013.01); *A61B 2562/046* (2013.01); *A61B 2562/14* (2013.01); *A61B 2562/164* (2013.01)

(58) Field of Classification Search
USPC ............................................ 381/67, 56, 423
See application file for complete search history.

(56) References Cited

U.S. PATENT DOCUMENTS

| | | | | |
|---|---|---|---|---|
| 7,165,451 | B1 * | 1/2007 | Brooks ................ | A61B 5/0093 |
| | | | | 73/579 |
| 7,857,763 | B2 * | 12/2010 | Tai ...................... | G01S 15/8979 |
| | | | | 600/459 |
| 9,078,571 | B2 * | 7/2015 | Bridger ................... | A61B 7/04 |
| 10,828,007 | B1 * | 11/2020 | Telfort ................ | A61B 5/6833 |
| 2008/0039753 | A1 * | 2/2008 | Zomorodian .......... | A61H 35/00 |
| | | | | 601/148 |
| 2008/0154144 | A1 * | 6/2008 | Unver ................... | A61B 8/488 |
| | | | | 600/528 |
| 2012/0088986 | A1 * | 4/2012 | David ................... | A61B 5/021 |
| | | | | 600/301 |
| 2014/0371632 | A1 * | 12/2014 | Al-Ali ................. | A61B 5/7415 |
| | | | | 600/586 |
| 2015/0257728 | A1 | 9/2015 | Ferzli et al. | |
| 2015/0289820 | A1 * | 10/2015 | Miller ................... | A61B 5/681 |
| | | | | 600/300 |
| 2019/0069873 | A1 * | 3/2019 | Copt ........................ | A61B 7/04 |
| 2019/0150756 | A1 * | 5/2019 | Lee ........................ | A61B 5/339 |
| 2020/0000371 | A1 | 1/2020 | Artunduaga | |
| 2021/0338189 | A1 * | 11/2021 | Vernalis ................. | A61B 7/04 |
| 2023/0210489 | A1 * | 7/2023 | Boese ..................... | A61B 7/04 |
| | | | | 600/586 |
| 2023/0233179 | A1 * | 7/2023 | Warner ................ | A61B 8/4236 |
| | | | | 600/454 |
| 2024/0000381 | A1 * | 1/2024 | Andino ............... | A61B 5/6804 |
| 2024/0023817 | A1 * | 1/2024 | Vajdic ................... | A61B 5/282 |
| 2024/0188906 | A1 * | 6/2024 | Seoane ................ | A61B 5/0006 |

* cited by examiner

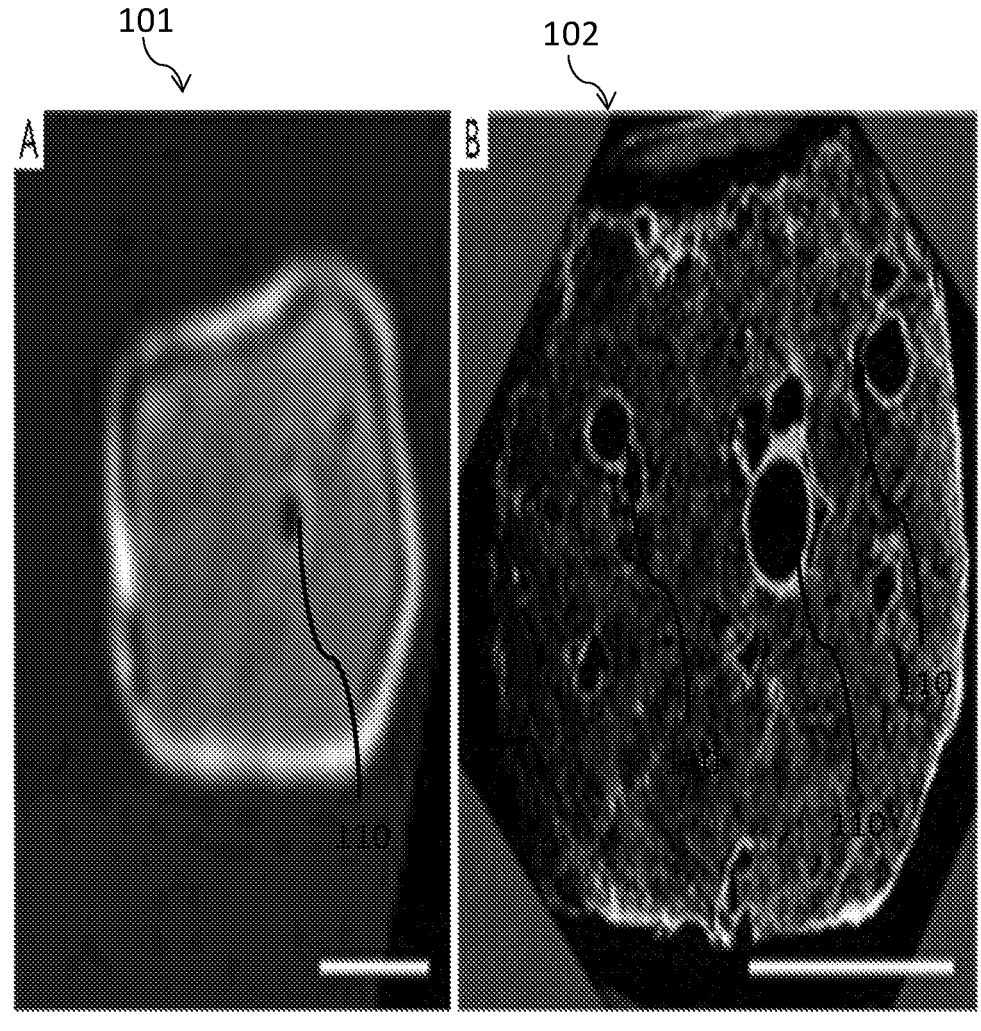
FIG. 1A                    FIG. 1B

103

201

202

220A

220B

220C

302

302

330

224

316

321

302

222    213A    330    305    213B    227

270

270    270

270

303

303

304

304

203, 301, 302, 303, or 304

400

221     203, 301, 302, 303, or 304     231
415A 410A     410C     415A     415B
400     415C
405A
410B
425
405B     405C

501

502

10 breaths per minute
(fast)

601

602

12 breaths per minute (fast)

603

604

701

800

SYSTEMS, DEVICES, AND METHODS FOR PERFORMING ACTIVE AUSCULTATION AND DETECTING ACOUSTIC SIGNALS AND/OR SONIC ENERGY MEASUREMENTS

RELATED APPLICATION

This application is an international patent application of, and claims priority to, U.S. Provisional Patent Application No. 63/222,506 filed 19 Jul. 2021 and entitled "SYSTEMS, DEVICES, AND METHODS FOR PERFORMING ACTIVE AUSCULTATION AND DETECTING SONIC ENERGY MEASUREMENTS," which is incorporated herein in its entirety.

FIELD OF INVENTION

The present disclosure is related to systems, devices, and methods for performing active auscultation to determine conditions of organs within an animal body, typically the heart or lungs.

BACKGROUND

Many people have health issues related to the function of their internal organs. In particular, changes to internal air compartments of a person's lungs may provide critical insight as to when treatment may be needed, which may be monitored as air trapping. Air trapping, defined as an abnormal increase in the volume of air remaining in the lungs at the end of exhalation, is a key feature of chronic obstructive pulmonary disease (COPD). Many studies have now shown that air trapping is an earlier, more sensitive marker of lung dysfunction than conventional spirometric measures. For example, air trapping can be detected in people with normal spirometry and no COPD symptoms, who years later are diagnosed with COPD.

Auscultation is used to determine conditions of organs within an animal body, typically the heart or lungs. A signal is introduced into the body, often times, by manually tapping the chest or back. After that signal has interacted with the organ of interest (typically the lungs), it is detected by a stethoscope and interpreted by a medical practitioner. By analyzing the detected signal, conditions of the organ can be determined.

Importantly, monitoring air trapping in an accurate manner currently requires the active monitoring by a medical practitioner or an individual trained in determining irregular air trapping. This is particularly problematic because it makes day to day monitoring of a gradually worsening condition extremely difficult.

BRIEF DESCRIPTION OF THE DRAWINGS

The present invention is illustrated by way of example, and not limitation, in the figures of the accompanying drawings in which:

FIG. 1A provides an image of a scanned, relatively healthy lung with a small volume of air trapped therein which is shown in image 101 as a dark spot, in accordance with some embodiments of the present invention;

FIG. 1B provides an image of a scanned lung affected with COPD that includes a plurality of pockets, or volumes, of trapped air, in accordance with some embodiments of the present invention;

3

Figure 3A:
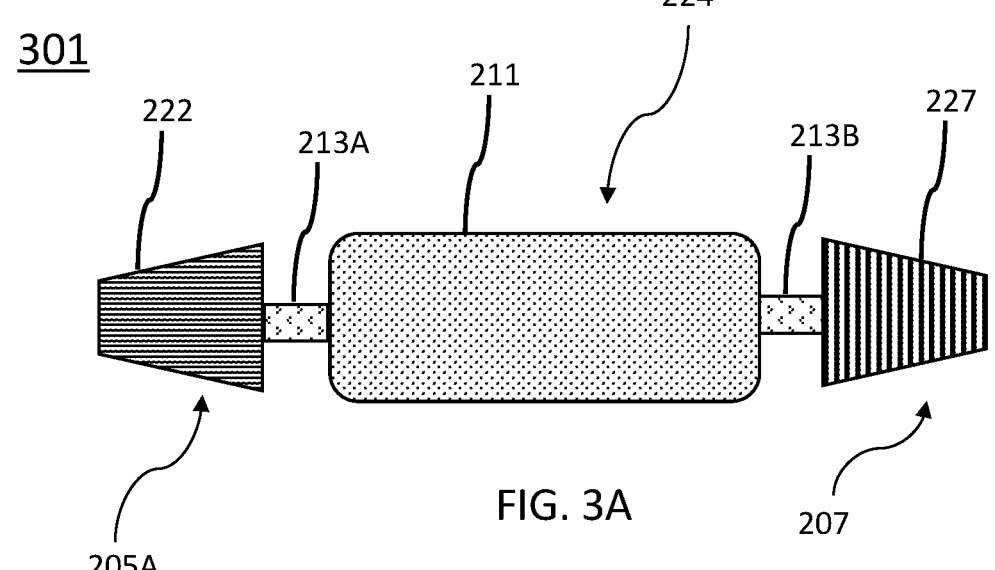
FIG. 3A is a top view of an exemplary active auscultation device, in accordance with some embodiments of the present invention.
Figure 3B:
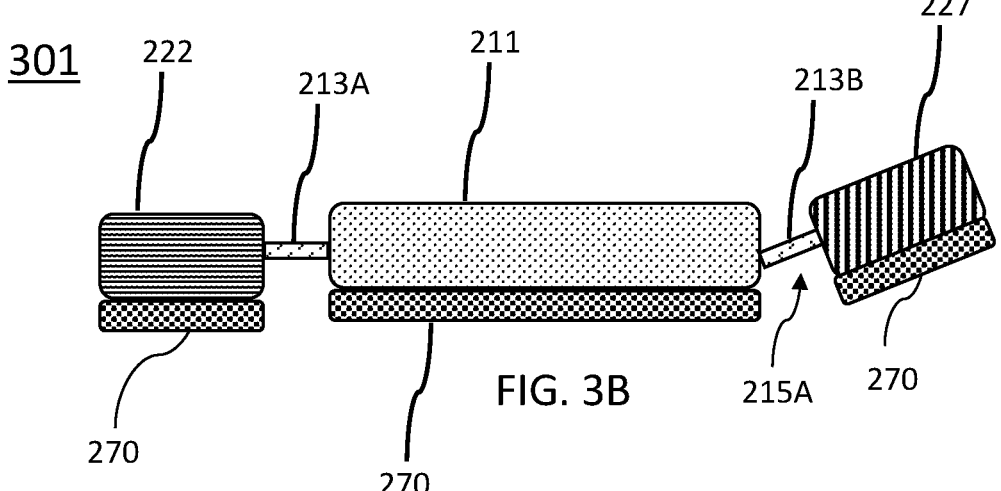
FIG. 3B is a side view of the exemplary active auscultation device of FIG. 3A, in accordance with some embodiments of the present invention.
Figure 3C:
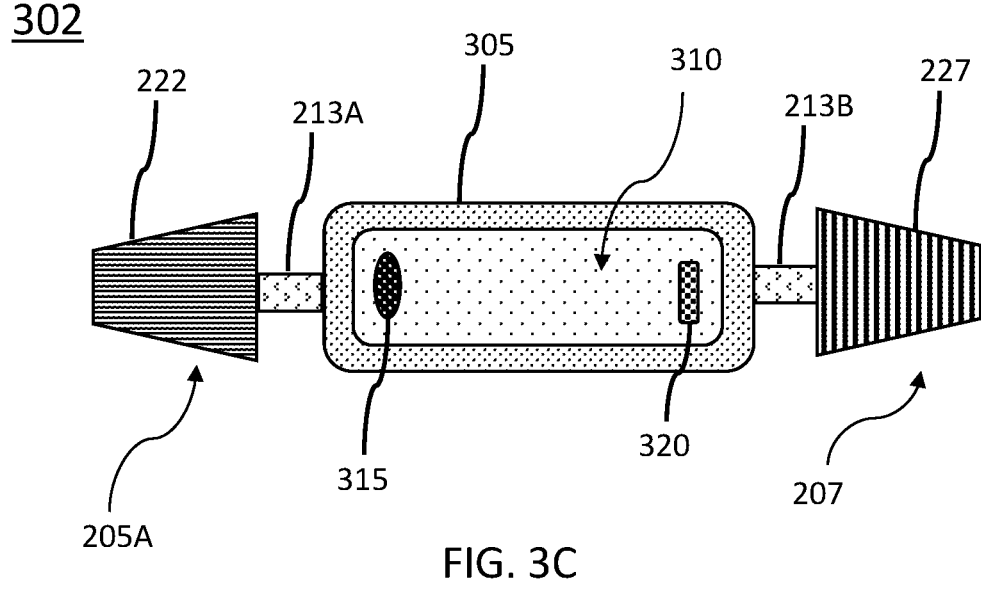
FIG. 3C is a top view of another exemplary active auscultation device with a removable main body not seated in a cradle, in accordance with some embodiments of the present invention.
Figure 3D:
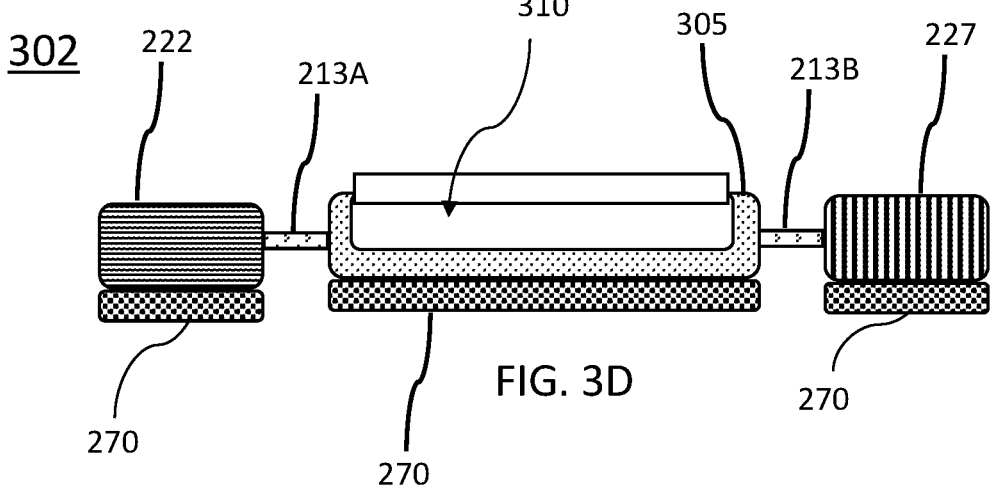
FIG. 3D is a side view the active auscultation device of FIG. 3C, in accordance with some embodiments of the present invention.
Figure 3E:
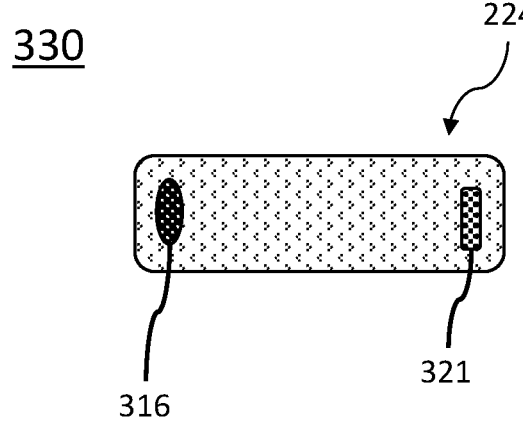
FIG. 3E is a bottom view of a removable main body housing, in accordance with some embodiments of the present invention.
Figure 3F:
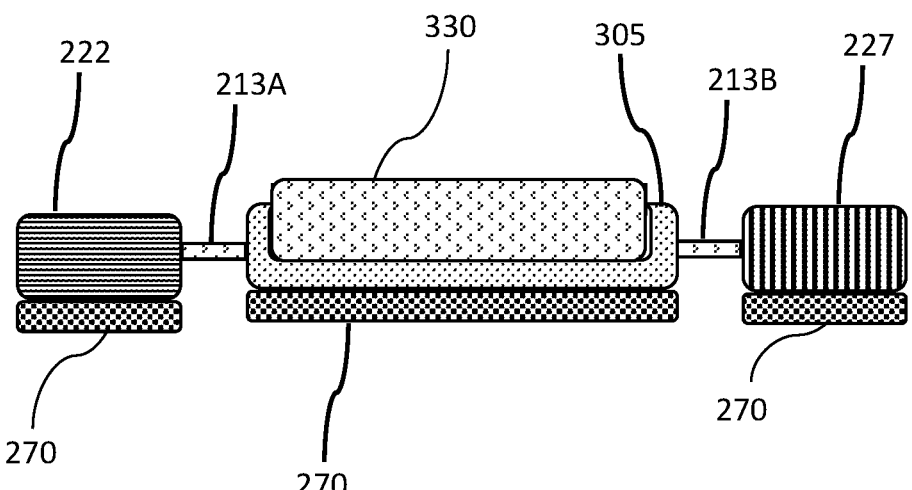
FIG. 3F is a side view the active auscultation device of FIG. 3C with the removable main body housing seated within the cradle, in accordance with some embodiments of the present invention.
Figure 3G:
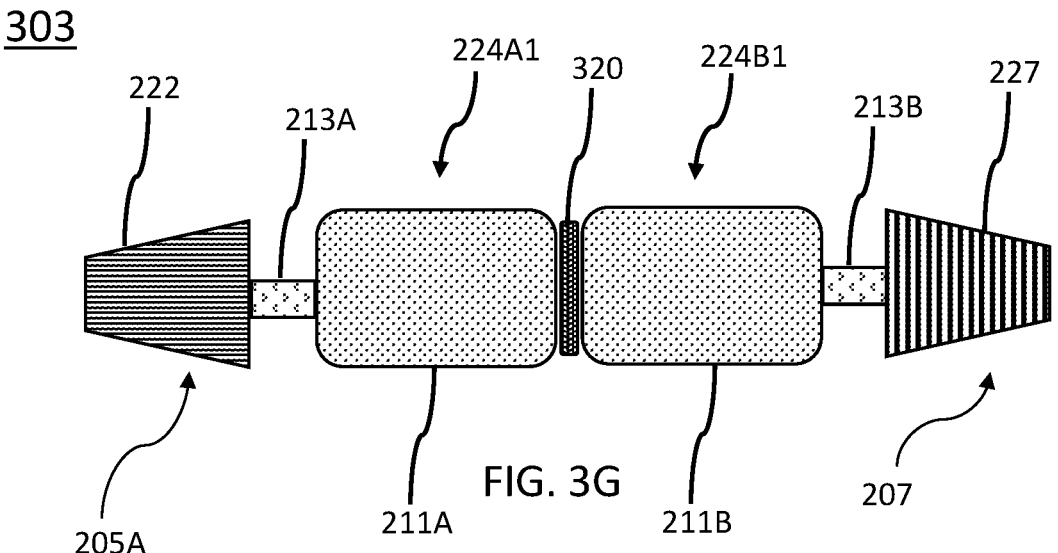
FIG. 3G is a top view of an exemplary hinged active auscultation device, in accordance with some embodiments of the present invention.
Figure 3H:
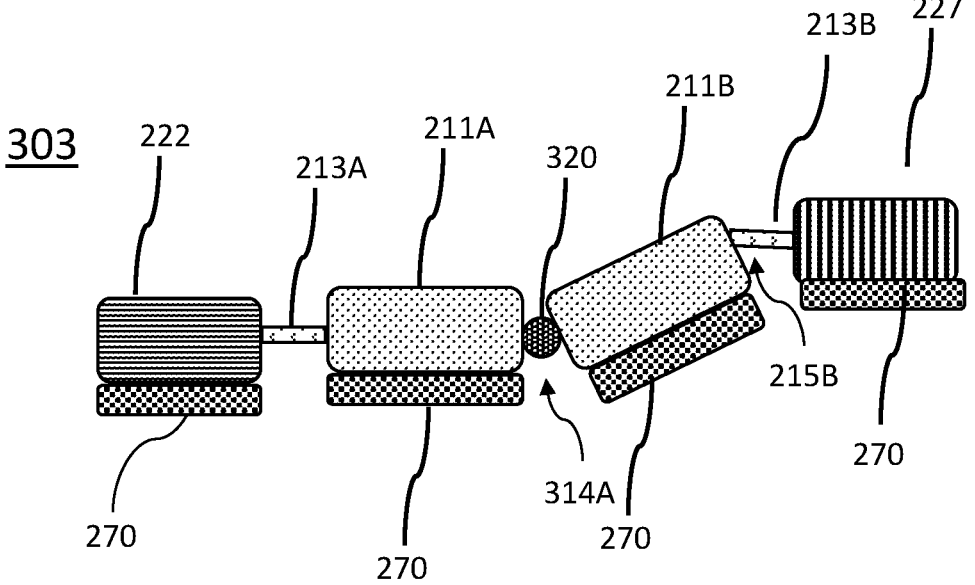
FIG. 3H is a side view the hinged active auscultation device of FIG. 3G, in accordance with some embodiments of the present invention.
Figure 3I:
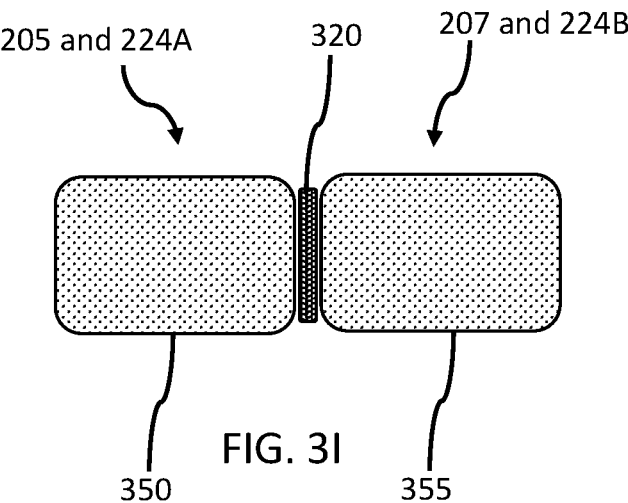
FIG. 3I is a top view of another exemplary hinged active auscultation device, in accordance with some embodiments of the present invention.
Figure 3J:
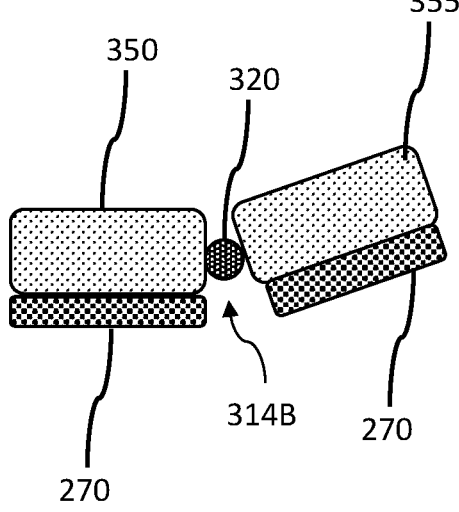
Figure 4A:
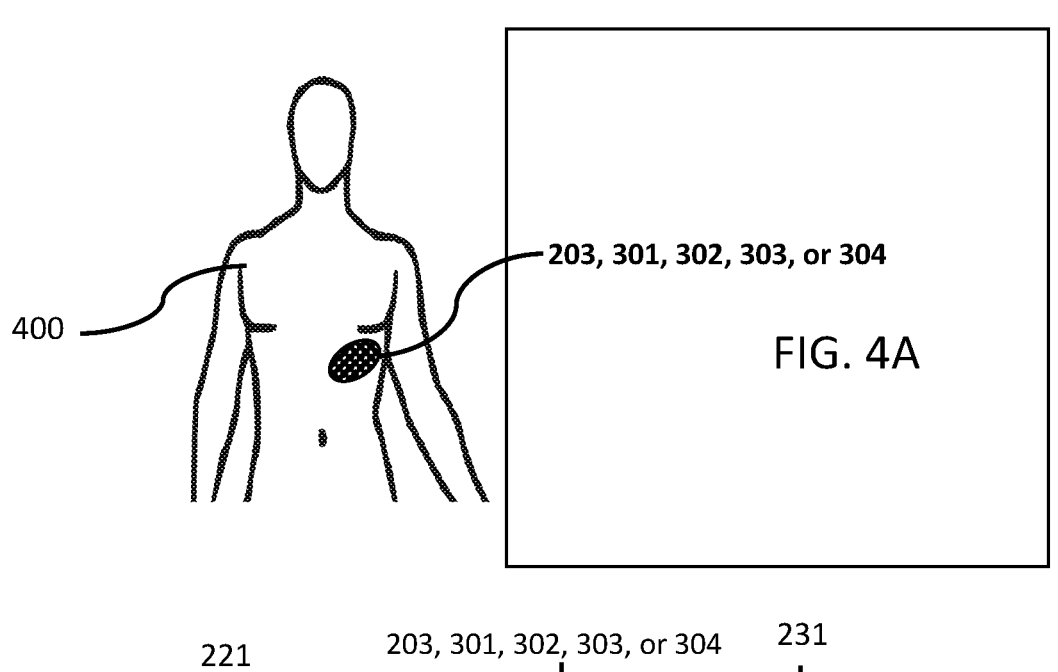
Figure 4B:
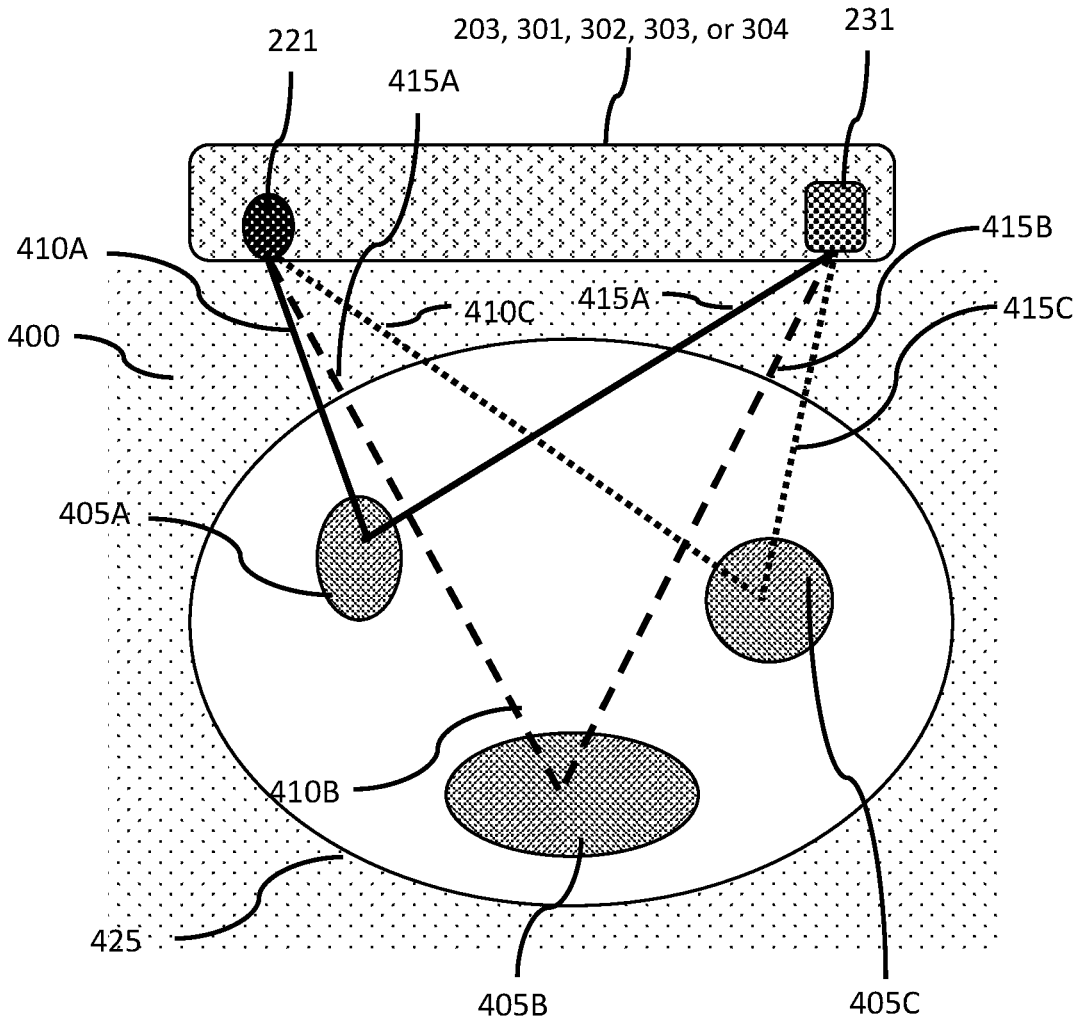
Figure 5A:
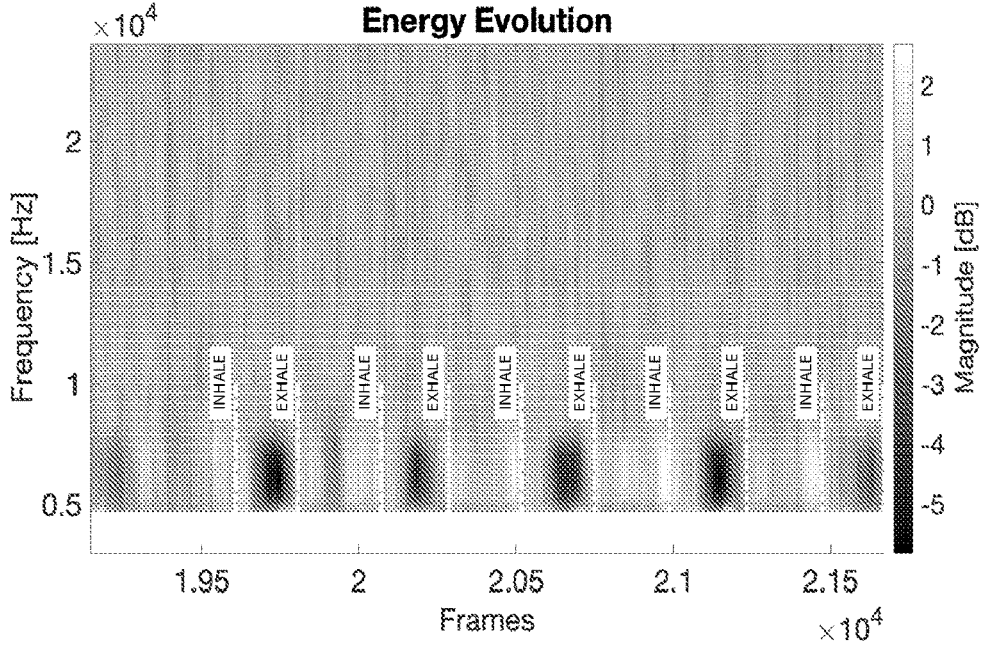
Figure 5B:
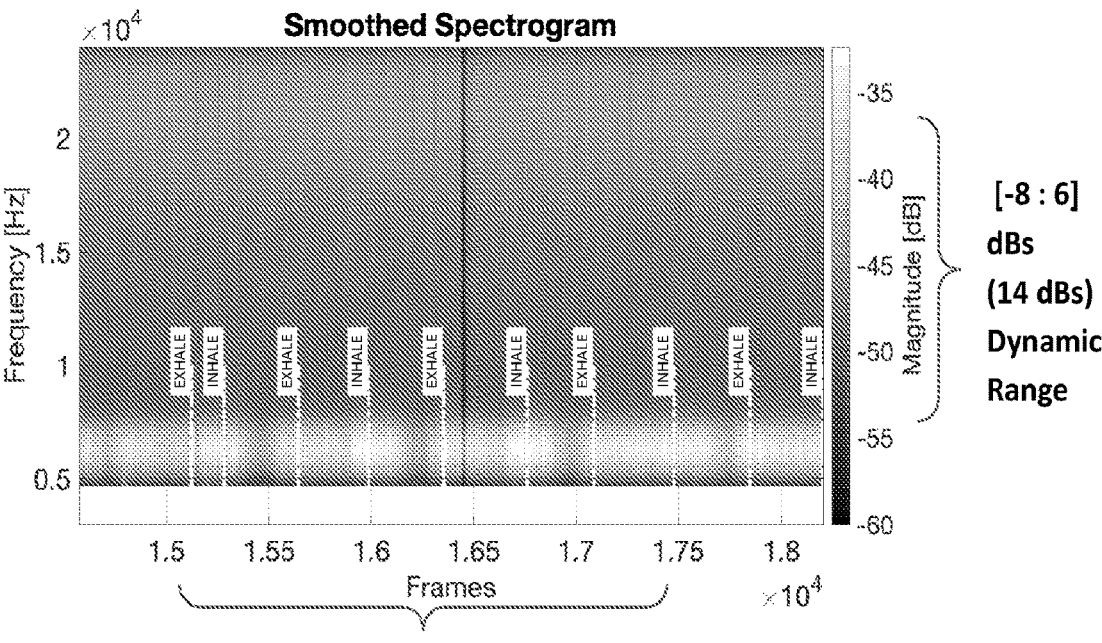
Figure 5C:
Figure 5C:
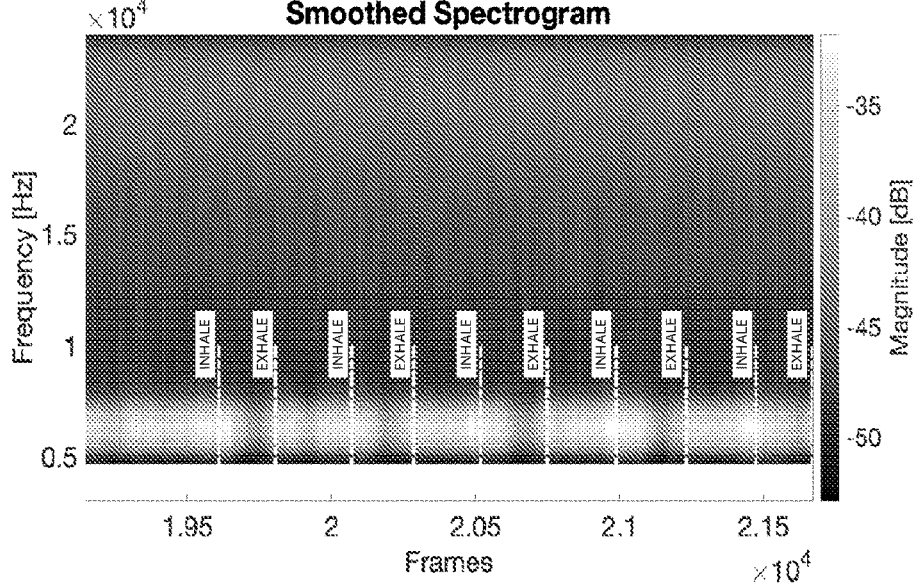
Figure 5D:
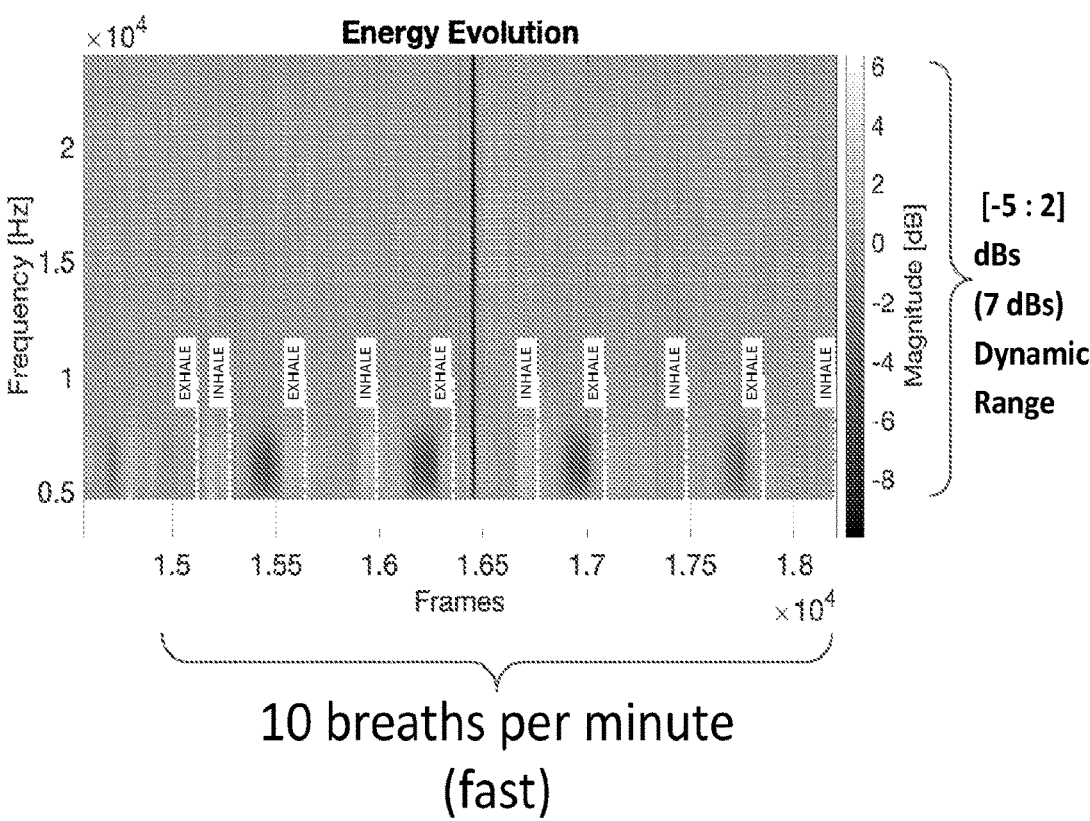
Figure 6A:
Figure 6A:
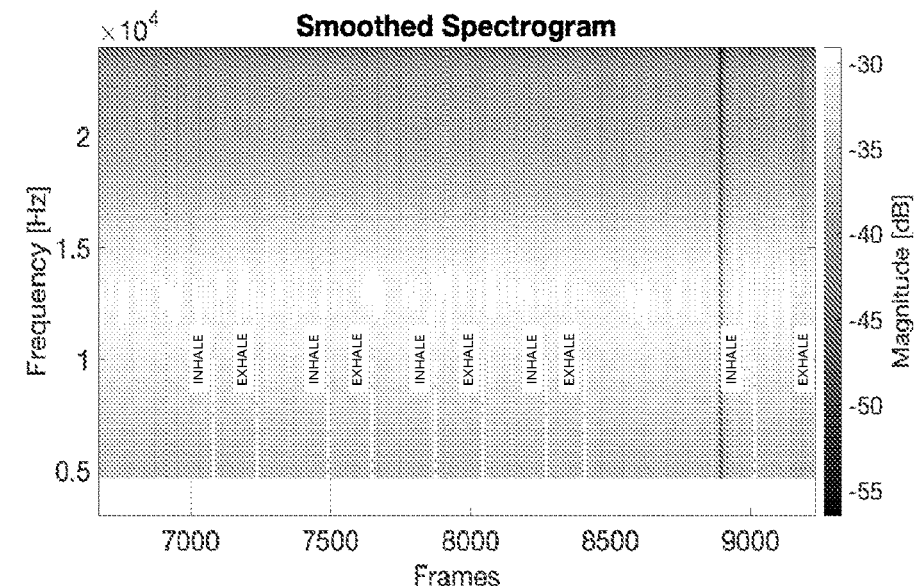
Figure 6B:
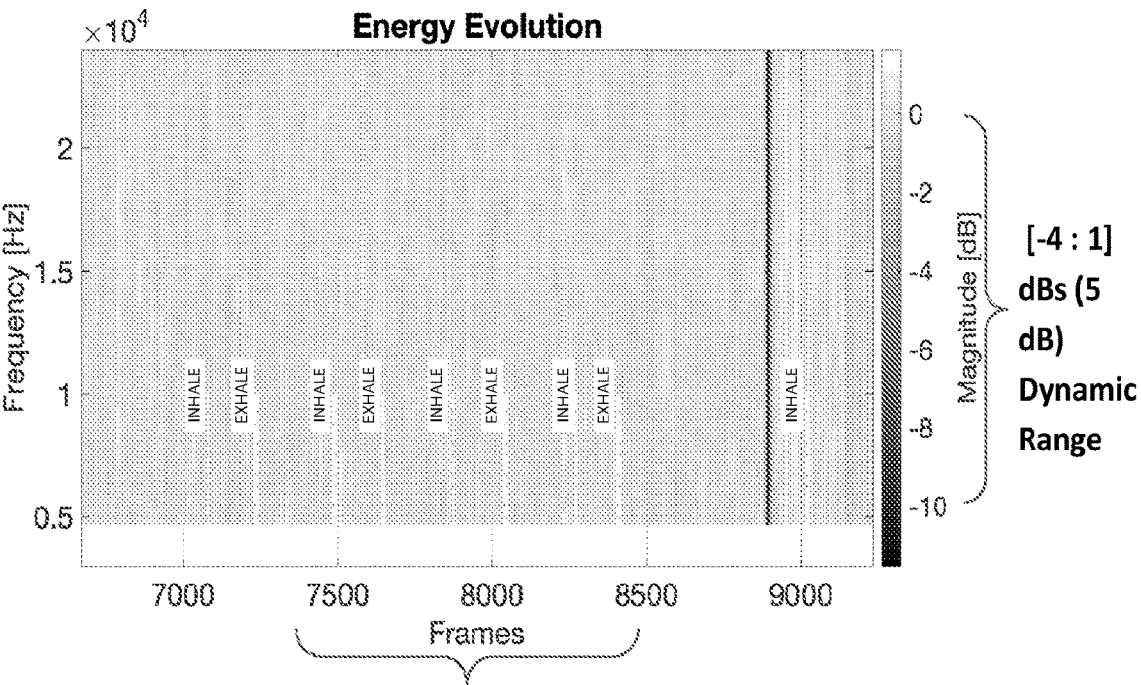
Figure 6C:
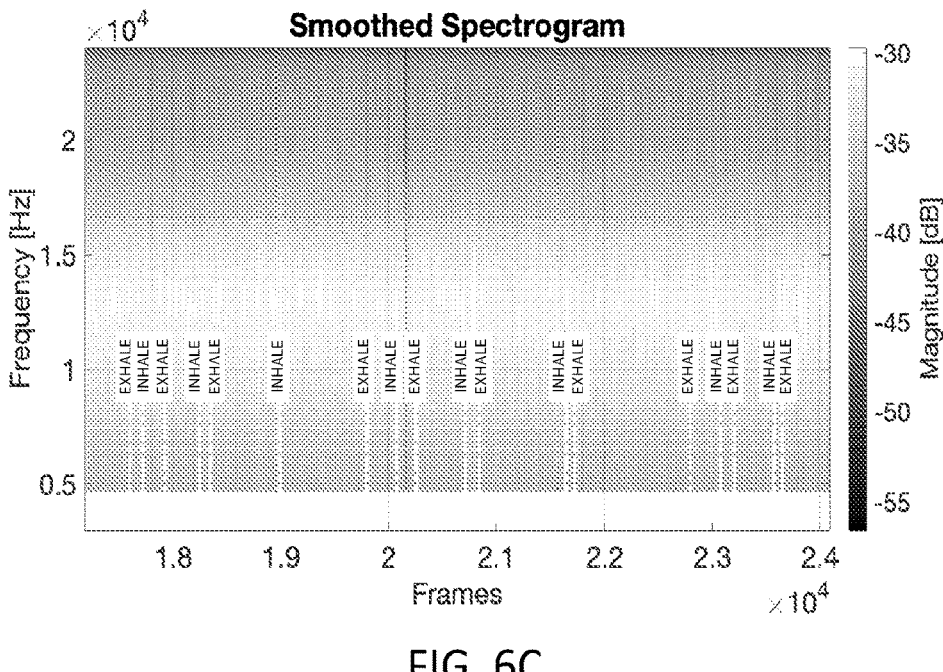
Figure 6D:
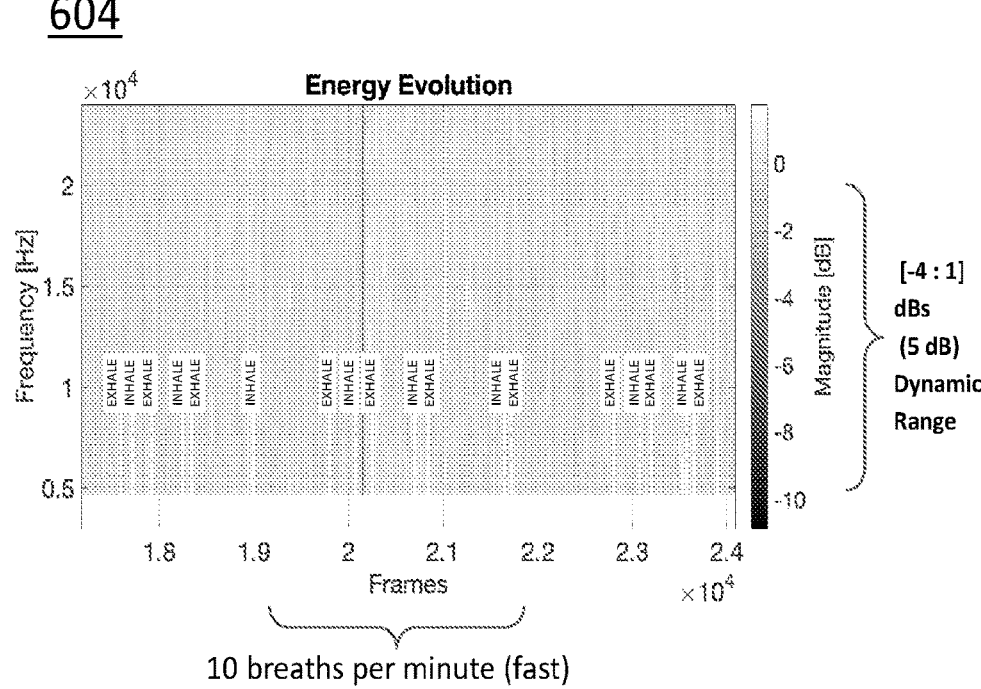
Figure 7:
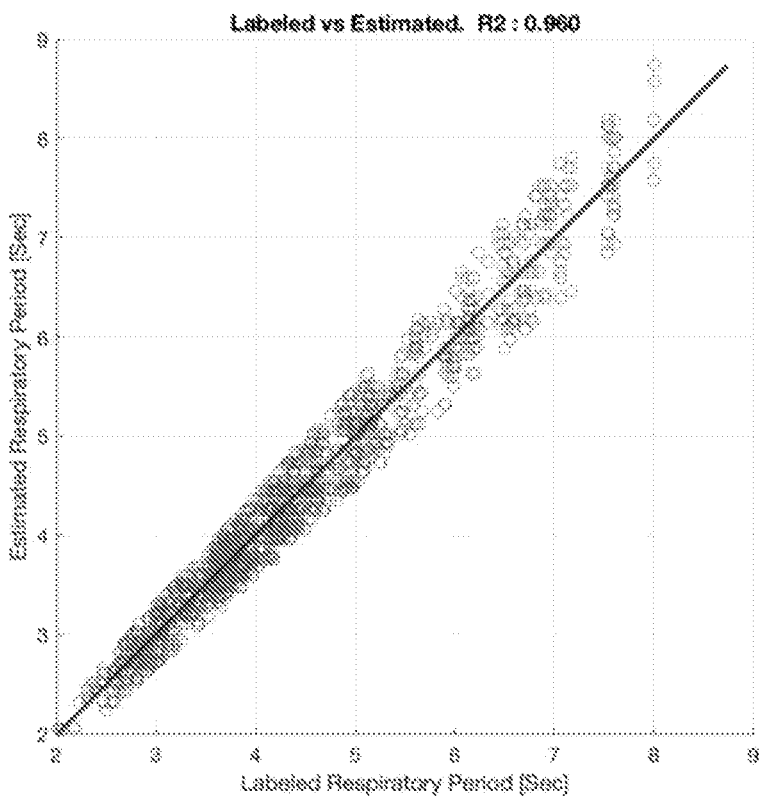
Figure 8:
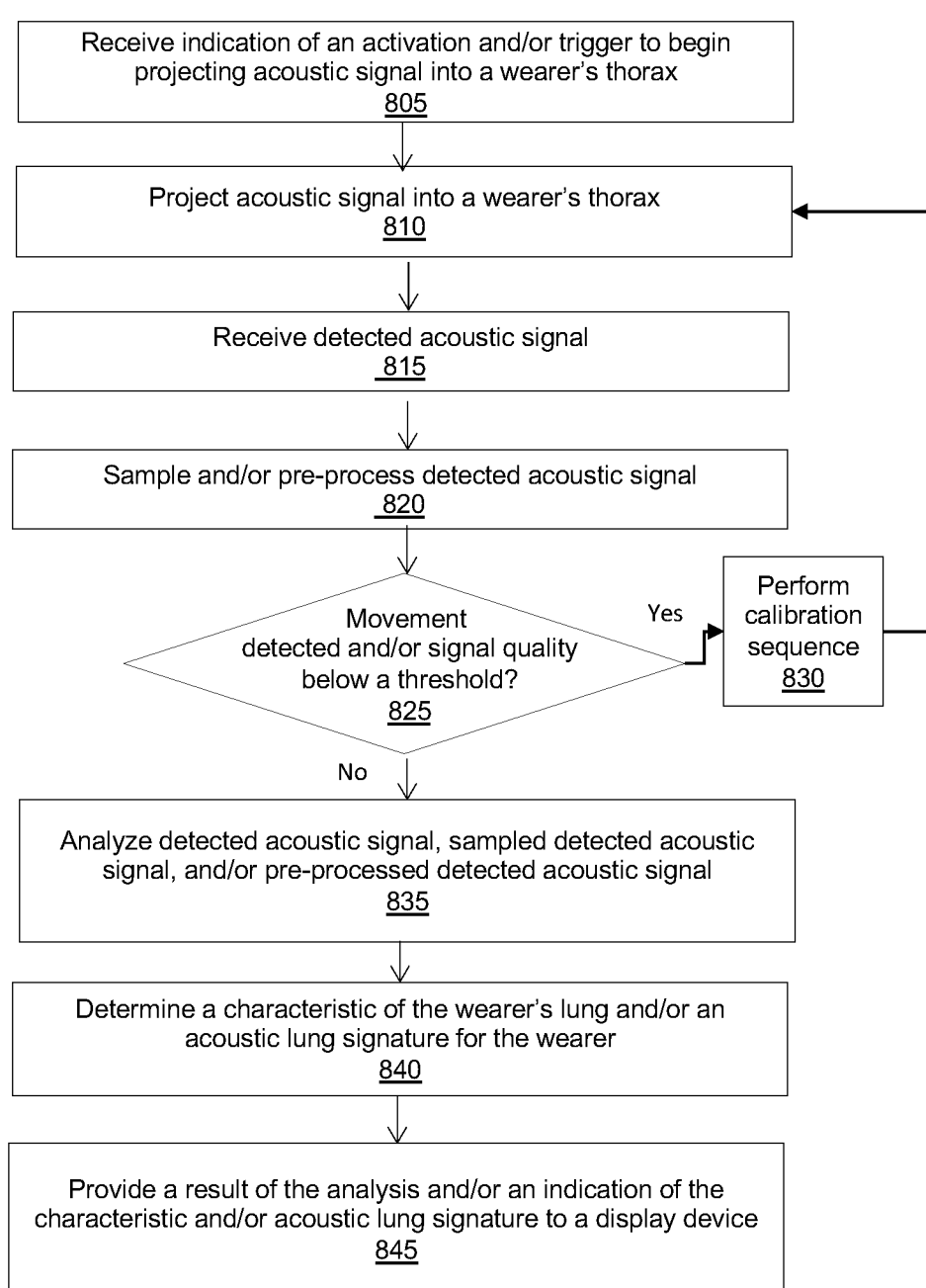

FIG. 3J is a side view the hinged active auscultation device of FIG. 3I, in accordance with some embodiments of the present invention;

FIG. 4A is a diagram of an exemplary wearer with an active auscultation device attached to his or her chest below the pectoral muscle, in accordance with some embodiments of the present invention;

FIG. 4B is a diagram of components of an exemplary active auscultation system in use to measure acoustic energy/waves emanating from an approximation the wearer's lung, in accordance with some embodiments of the present invention;

FIG. 5A provides a spectrogram of a detected acoustic signal from a wearer's lung that does not have COPD, in accordance with some embodiments of the present invention;

FIG. 5B provides a spectrogram of an energy change, or energy evolution, over time for the wearer of FIG. 5A, in accordance with some embodiments of the present invention;

FIG. 5C provides a smoothed spectrogram showing detected acoustic signals for the wearer of FIG. 5A when she has increased her respiratory rate to 12 breaths per minute, in accordance with some embodiments of the present invention;

FIG. 5D provides another spectrogram an exemplary reduced dynamic range of the energy evolution for the detected acoustic signals, in accordance with some embodiments of the present invention;

FIG. 6A provides a smoothed spectrogram of detected acoustic signals from a wearer's lung when the wearer is breathing at a rate of approximately 12 breaths per minute and the lung has severe COPD, in accordance with some embodiments of the present invention;

FIG. 6B is a spectrogram showing a reduced dynamic range [−4:1] dB of the wearer's lung from FIG. 6A, in accordance with some embodiments of the present invention;

FIG. 6C is a spectrogram showing detected acoustic signals when a respiratory rate of the wearer of FIG. 6A is increased, in accordance with some embodiments of the present invention;

FIG. 6D is a spectrogram showing detected acoustic signals when the wearer of FIG. 6A when the respiratory rate of the wearer has decreased to 10 breaths per minute, in accordance with some embodiments of the present invention;

FIG. 7 is a scatter graph comparing labeled respiratory periods with estimated respiratory events, in accordance with some embodiments of the present invention; and FIG. 8 is a flowchart providing the steps of an exemplary process for performing active auscultation, in accordance with some embodiments of the present invention.

Throughout the drawings, the same reference numerals and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

SUMMARY

The present disclosure is directed to a device configured to measure air pockets contained within the body and/or tissue (e.g., lung tissue) of an individual. In one embodiment, a signal, such as a sound wave of one or more frequencies, may be projected into the individual and respondent acoustic signals may be detected by a microphone and measured such that, for example, refraction and reflection of the incident signal may be measured or otherwise determined. In some embodiments, this may allow measurement and monitoring of air pockets within the body of an individual. In some embodiments, the device may also be configured to receive and store measurements relating to signal emission, reflection, and refraction. In some embodiments, the device may comprise a power source and memory module sufficient to record data of a set period of time, wherein the set period of time corresponds to the time between data upload/download to an external device as described hereinbelow.

In some embodiments, the device of the present disclosure may be in electronic communication with a separate or external electronic device, such as by a wireless electronic communication method. Some wireless electronic communication methods may include, Bluetooth, Wi-Fi communications, and other wireless signals. In one embodiment, the external electronic device may be a smart phone, tablet, or other smart device. In some embodiments, the device of the present disclosure may communicate with an external electronic device via the internet, an intranet, or any other network communication protocol.

One embodiment may be a device for performing active auscultation comprising: a main body; a body attachment structure; and one or more wings; wherein said main body comprises a memory, battery, IMU, transceiver, and DSP; wherein said one or more wings comprise a microphone wing and a speaker wing; wherein said microphone wing comprises one or more microphones; wherein said speaker wing comprises a speaker; wherein said one or more wings comprise one or more sensors and/or devices such as a temperature sensor, an electrocardiogram device, blood oxygenation sensor, a oximeter, a tissue oxygenation sensor, a skin conductivity sensor; wherein said main body is configured to engage said body attachment structure; wherein said body attachment structured is configured to engage, on a first side said main body, and on a second side an animal body.

In some embodiments, the device for performing active auscultation may be affixed to an individual's body and may periodically record high resolution and/or low resolution data measurements. In some embodiments, the data recorded by the device for performing active auscultation may be transmitted via a wireless communication method to a separate electronic device, such as a cell phone. In a preferred embodiment, the device may record as much data, in as high a quality, as may be allowable based on, for example, a capacity of the battery and memory units.

In some embodiments, sensor data for a wearer may be collected over time and subsequently detected sensor data may be compared with previously detected sensor data to determine differences therebetween which may be indicative of, for example, an improving or declining medical condition for the wearer. Additionally, or alternatively, one or more characteristics of the sensor data may be determined and these characteristics may be compared to one another and/or a predetermined value for the characteristic in order to determine, for example, how the wearer's characteristic compares with other characteristics in order to deduce a similarity or pattern which may be used to diagnose the wearer and/or predict when an adverse event for the wearer is likely to occur.

Additionally, or alternatively, in some instances, a duration, an intensity, and/or frequencies included in the signal may be adjusted responsively to, for example, the determined characteristics of the received acoustic signal and/or a lack of a sufficiently clear received acoustic signal.

A device for performing active auscultation may include a microphone wing housing, a speaker wing housing, and a main body housing. A surface of the microphone wing housing, speaker wing housing, and/or main body housing may be configured to be mechanically and/or acoustically coupled to the patient's skin via, for example, an adhesive, an elastic band, a sleeve, and/or a garment (e.g., the device is integrated into fabric for a shirt or bra).

The speaker wing housing may house a speaker, or a speaker array configured to project one or more acoustic signal(s) into a patient's skin toward target tissue such as a lung, or a region of a lung, responsively to receipt of an instruction and/or electrical signal from a controller.

The microphone wing housing may house a microphone or microphone array configured to detect a detected acoustic signal emanating from the patient's skin and underlying target tissue and communicate the detected acoustic signal to the controller.

The main body housing may be physically, electrically, and/or communicatively coupled to the microphone wing housing and/or components housed therein via a first flexible coupling and physically, electrically, and/or mechanically coupled to the speaker wing housing and/or components stored therein via a second flexible coupling. The main body housing may include a transceiver, a memory, the controller, and a battery.

The transceiver may be communicatively coupled to the controller and the memory and may be configured to communicate the detected acoustic signal to an external device and receive instructions from the external device. The memory may be communicatively coupled to the controller and the transceiver and may be configured, or programmed, to receive instructions from the transceiver and store a set of instructions for execution by the controller and store one or more measurements taken by the device and/or a component thereof. The controller may be configured, or programmed, to generate an electrical signal responsively to an instruction stored in the memory and communicate the electrical signal to the speaker, receive the detected acoustic signal from the microphone and communicate the detected acoustic signal to the transceiver. In some embodiments, the controller is further configured to pre-process the detected acoustic signal to remove noise prior to, for example, communication to the transceiver. The battery may be electrically coupled to the speaker, the microphone, the transceiver, the memory, and the controller and may be configured to provide electrical power thereto.

Systems, devices, and/or methods for performing active auscultation disclosed herein may be configured, or programmed, to receive a first detected acoustic signal or set of dets that may correspond to a first incident acoustic signal projected into the thorax of a wearer of an active auscultation device that includes at least one speaker and one microphone. Optionally, an indication that the wearer has moved may be received and performance of a calibration sequence for the active auscultation device (e.g., the microphone(s) and/or speaker(s) included in the active auscultation device) may be initiated responsively to receipt of the indication that the wearer has moved. Movement of the user may be detected by, for example, a motion sensor or inertial movement unit resident within and/or coupled to the active auscultation device. Movements include, but are not limited to, the wearer breathing, walking, or shifting position (e.g., turning over in bed).

A second detected acoustic signal may also be received. The second detected acoustic signal may correspond to a second incident acoustic signal projected into the thorax of the wearer of the active auscultation device. The second detected acoustic signal and the second incident acoustic signal be different from the respective first detected acoustic signal and the first incident acoustic signal due to performance of the calibration sequence.

The first and second detected acoustic signals may be processed and/or analyzed to determine one or more characteristics of a wearer's lung, lung region, and/or both lungs based upon the analysis. An indication of the characteristic may then be provided to a user via, for example, a display of a computer device. In some embodiments, this characteristic may be compared with a previously determined characteristic of the same, or a different, type of the wearer's lung to determine differences therebetween. The previously determined characteristic may have been determined at any prior point in time (e.g., 10 s, 20 minutes, or 1 year) so that characteristics of the wearer's lungs may be compared with one another in order to assess changes thereof. These changes may occur on a second-by-second, minute-by-minute (e.g., before and after respiratory therapy or performance of an exercise) day-by-day, month-by-month, and/or year-by-year (as part of, for example, an annual physical exam) so that the wearer's lungs may be monitored on a frequency/schedule that may yield meaningful assessment, monitoring, and/or diagnosis of the wearer's lung and/or respiratory health over time and/or in different situations and/or from different angles.

Exemplary determined and/or previously determined characteristics of the wearer's lung include an acoustic lung signature, a volume of air trapped in the wearer's lung, a number of pockets of trapped air present in the wearer's lung, a size of one or more pockets of trapped air present in the wearer's lung, a position of one or more pockets of trapped air present in the wearer's lung.

Written Description

COPD is an umbrella term for heterogeneous disease or medical condition that effects the lungs. Patients diagnosed with COPD may have a variety of different phenotypes (clinical features) and endotypes (physio-pathological causes) that can serve the operational definition of COPD, which is typically diagnosed when a patient exhibits lung obstruction via a spirometry measurement of a ratio of forced expiratory volume for one second (FEV1) and expiratory forced vital capacity (FVC) value of, or below, 0.7, a response to relevant exposure to pollutants (tobacco, indoor household, air), and/or respiratory symptoms (dyspnea, cough, sputum production). Because COPD can encompass such a wide range of symptoms and causes, patients may exhibit a wide range of disease severity, with drastically different functional status, quality of life compromise, clinical needs, and prognosis, despite having similar background, exposure history, and/or spirometric affectation.

Exacerbations of COPD may be defined as a clinically evident and sustained increase in symptom severity that exerts the need for a change in and/or an addition of one or more medical treatments and/or interventions. Exacerbations of COPD are fairly common for COPD patients and contribute to short-term and long-term patient prognosis and deterioration of patient respiratory health and general well-being. In addition, treatment of exacerbations account for a high share of the total cost of caring for COPD patients, especially when that care requires in-hospital treatment. Moreover, exacerbations may be present even in patients with mild obstruction/mild COPD and an exacerbator, which may be defined as a patient having two or more episodes of exacerbation or one needing hospitalization in a year, may behave like a stable phenotype susceptible to, for example, a treatable trait approach.

At present, there is no clinically available biomarker that can predict, early and in an accurate fashion, the onset and/or occurrence of a COPD exacerbation. Spirometry is the most widely pulmonary function test in use for confirmation of obstructive lung diseases but, it has many caveats and disadvantages. For example, for spirometry to provide an accurate measure of lung function, or obstruction, the spirometry typically needs to be performed in pulmonary function test laboratory or doctor's office by sufficiently trained personnel and may require the use of expensive equipment. Thus, spirometry measurements are difficult to execute in the home even with trained professionals administering the tests and are not a suitable tool for frequent (e.g., daily or weekly) lung function testing. In addition, the measured values for FEV1 provided by traditional spirometry methods have poor (if any) correlation with dyspnea, treatment efficacy, COPD exacerbations, and/or mortality events and cannot detect or predict the early onset of an exacerbation or declines in lung function. Thus, in order to accurately monitor a COPD or respiratory patient, additional measurements (body-mass index, an index of airflow obstruction, dyspnea, and exercise (BODE), an index of age, dyspnea and obstruction (ADO) index, and/or a classification of global initiative for chronic obstructive lung disease (GOLD) classification) of lung function are often required.

However, measurement and/or analysis of other biomarkers, physiological variables, and/or image-based measurements of lung health may perform as surrogates of prognosis and symptoms. One biomarker of interest is lung hyperinflation (LH), which is often caused by air trapping. Air trapping may be understood as a volume of air that remains in the lung after a thorough exhalation. Trapped air may be contained with discrete pockets of lung tissue following a patient's thorough exhalation. Most COPD patients suffer from/exhibit some degree of air trapping regardless of the COPD's severity, endotype, or phenotype and, at times, the air trapping may even precede symptoms or spirometric changes in diagnosed/exposed individuals. Thus, the monitoring of air trapped in a patient's lungs can provide valuable information regarding disease state, respiratory health, and/or patient wellbeing.

In many cases, air trapping is a heterogeneous process that intertwines at least two anatomical and physiological components: 1) a partially irreversible and progressive gas trapping in disrupted lung tissue or emphysema and 2) a more dynamic and potentially reversible gas trapping caused by small airway dysfunction. These components (and a volume of air trapped in pockets of lung tissue overall) are affected in different proportions in each patient by, for example, continuous insult, senescence, medication, exercise, and exacerbation.

Air trapping may be caused by a variety of phenomena. For example, on some occasions, air trapping may be caused by the loss of elastic recoil of the lung parenchyma that is associated with tissue destruction in emphysema and/or the narrowing of terminal airways as seen in, for example, chronic bronchitis. Some patients exhibit air trapping without having emphysema and other patients exhibit air trapping along with predominant emphysema. In this latter group (air trapping and emphysema), there are two primary phenotypes: homogenous emphysema and upper lobe predominant emphysema.

Often times, air trapping in COPD patients is heterogeneous in terms of an anatomical phenotype (e.g., upper lobe predominance vs homogenous emphysema) and physiological terms (associated with emphysema and/or with small airway disease) and that a pattern of air trapping and/or pockets of trapped air encountered in a COPD patent may be used to roughly determine a prognosis for these patients. In other cases, air trapping (or trapped air pockets) may be diffusely present throughout the entire pulmonary anatomy.

On some occasions, air trapping may be defined as an augmented relationship between residual lung volume and total lung capacity (RV/TLC) that has been traditionally measured using even more complex and costly techniques than spirometry, such plethysmography, gas dilution techniques, and chest tomography. However, the complexity and financial cost of using these techniques limits their reach to highly selected cohorts able to visit specialized health care centers and are rarely available for large populations of patients and the general public.

In addition, air trapping correlates well with dyspnea at rest and during exercise, and it also appears early in the course of an exacerbation. Thus, measurements of air trapping may be correlated with disease progression for dyspnea as well as COPD.

Thus, there is an urgent need for practical physiological biomarkers that can overcome the stated limitations of spirometry and can serve as a guideline for personalized treatment. There is further a need for an instrument that can work as an early predictor of exacerbations, in order to avoid death, deterioration of functionality and quality of life, and reduce the economic costs associated with caring for COPD patient and in particular the treatment of exacerbations within the COPD population. This need may be met with the systems, devices, and methods disclosed herein, which are configured to, among other things, monitor volumes of trapped air within a wearer's lungs over short (e.g., minutes or hours) and long (e.g., hours, days, weeks, or months) durations of time without requiring expensive equipment or highly trained personnel to operate the devices/systems. The systems and devices disclosed herein may be used to, for example, determine short- and/or long-term trends of air trapping and other pulmonary health measurements in response to, for example, external stimulus and/or physical exertion exhibited by patients and to alert early deviation in tendencies in, for example, a day-to-day fashion so that, for example, COPD may be proactively managed in certain populations and/or exacerbations of COPD may be avoided.

Acoustic resonance is the ability of an object or system (e.g., a physical object such as an individual's body, body part (e.g., lung), or portion thereof) to amplify sound waves at frequencies that match one or more of the system's natural vibration frequencies. If the object is excited with energy at frequencies unrelated to their natural vibration frequencies, the energy will quickly dissipate. However, when the excitation approximates one of the object's natural vibration frequencies, the object will start to resonate and vibrate strongly at this frequency. An object's resonant frequencies are commonly identified by exciting the object with a broadband signal (i.e., noise composed of many frequencies) a pseudo-randomly generated frequency or range of frequencies, a chirp signal (a high-intensity and short duration acoustic signal), and/or a white noise signal. In most cases, the object resonates in the lowest natural frequency or an integer multiple of it.

Air trapping, or trapped air, may be defined as an abnormal increase in the volume of air remaining in the lungs, sometimes within discrete pockets of lung tissue, at the end of exhalation and it is a key feature of COPD. Many studies have now shown that air trapping is an earlier, more sensitive marker of lung dysfunction than conventional spirometric measures for conditions such as COPD. For example, air trapping can be detected in people with normal spirometry and no COPD symptoms who years later are diagnosed with COPD. A degree, or volume, of air trapped in a wearer/user's lung may be referred to herein as an air trapped index.

FIG. 1A provides an image 101 of a scanned, relatively healthy lung with a small volume of air trapped in a pocket therein which is shown in image 101 as a dark spot 110. FIG. 1B provides an image 102 of a scanned lung affected with COPD that includes a plurality of pockets, or volumes, of trapped air, which are shown in image 102 as a plurality of dark spots 110. Images 101 and 102 include a 1 cm scale bar to illustrate a size of the dark spots/trapped air pockets 110.

Figure 1C:
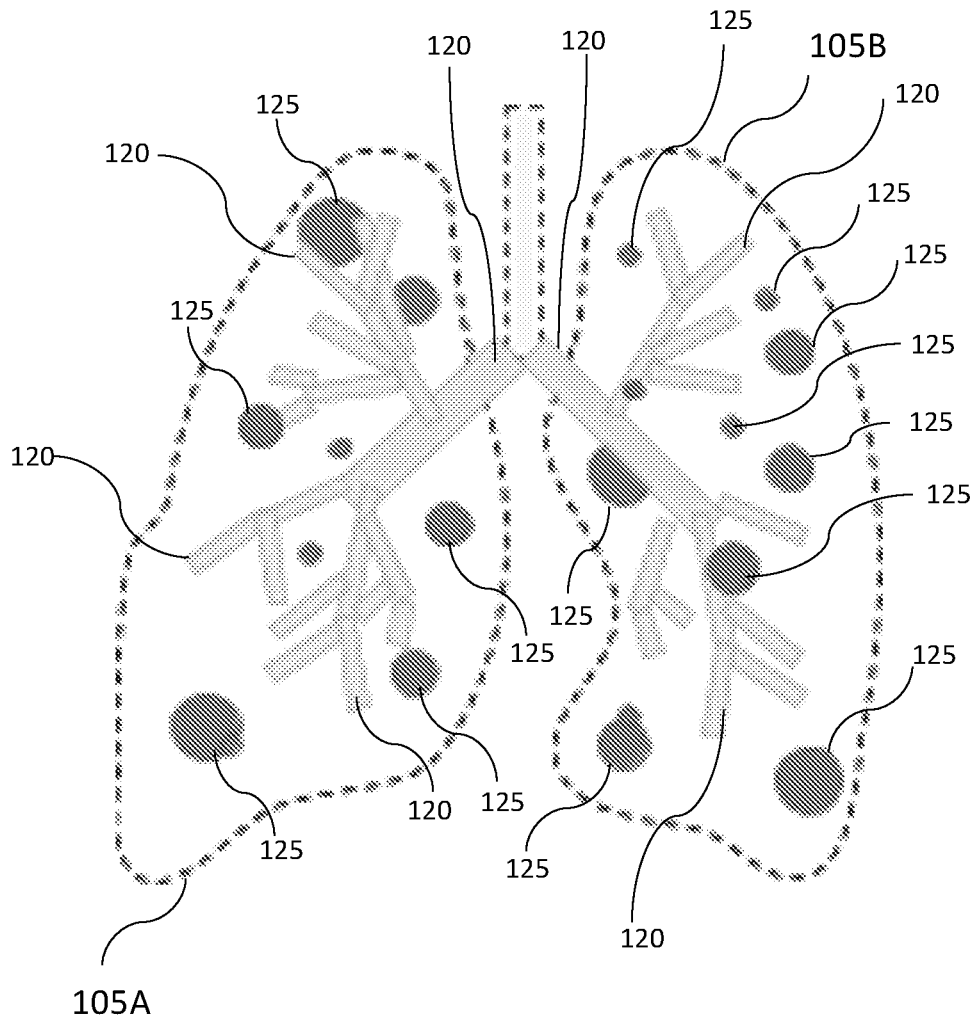
FIG. 1C provides a diagram of a model of an exemplary manner in which a left and right lung may be modeled or approximated, in accordance with some embodiments of the present invention.

FIG. 1C provides a diagram of a model 103 of an exemplary manner in which a left lung 105A and right lung 105B may be modeled or approximated. Model 103 represents the bronchial airways with a plurality of tubes 120 that have one or two open ends and volumes of trapped air as circles 125 that may represent spherical, or approximately spherical, volumes/pockets of trapped air (which may be referred to herein as "air pockets"). A model like model 103 may be generated without dividing the lungs into one or more lobes. Additionally, or alternatively, a model like model 103 may be generated by dividing the lungs into two or more lobes and/or grouping tubes and spheres by lobe, or location, within the lung. The model shown in FIG. 1C may be based on, for example, an image like images 101 and/or 102 that shows pockets of trapped air and/or other information regarding a lung such as multiple X-ray images of a lung taken from different angles, MRI images, CT scan images, PET scan images, and the like. With model 103, the naturally occurring resonant frequencies of lungs 105A and/or 105B and/or the trapped air volumes 125 may occur within the range of 2,000 Hz to 30,000 Hz, with the bulk of them in the range of 6,000 Hz to 15,000 Hz.

Disclosed herein are systems, devices, and methods that use acoustic energy/signals, to measure, store, and/or report information regarding a response of tissue and gasses within the tissue (e.g., air trapped in discrete pockets of tissue, or trapped air) to acoustic energy/signals. In many cases, acoustic energy is projected into an individual's body (typically the thorax) via an emitter like a speaker and resulting acoustic waves/energy are detected by, for example, a detector like a microphone. The detected acoustic waves/energy are analyzed to determine characteristics (e.g., quantity, size, volume, composition, location) of pockets of gas/air trapped in lung and other organ tissue.

In some instances, the acoustic waves/energy projected into the body may be of a particular frequency or set of frequencies (e.g., a narrowband or broadband spectrum). Sets of frequencies for projection into the body may be randomly and/or pseudo-randomly selected. At times, the acoustic energy may be a set of frequencies corresponding to low-frequency ultrasound, which in the case of COPD and/or air trapping may yield more accurate results for assessing lung health and/or air trapping than the standard of care for monitoring lung health (e.g., plethysmography). In some cases, the devices and methods disclosed herein may be configured to detect and/or monitor air pockets, or volume(s) trapped air that are too small to be detected by standard methods of assessing lung health. For example, in some situations, the lungs of and/or patients with early-stage COPD may be able to compensate for diminished breathing capacity caused by the early-stage COPD by breathing deeper and/or faster. In these situations, standard methods of assessing lung health may not detect the early-stage COPD and/or small volume(s) of trapped air, which leads to undiagnosed COPD and/or administration of effective early-intervention treatment.

The devices disclosed herein may include one or more acoustic energy emitters or speakers, that may be for example, low-frequency sound emitters, and one or more acoustic detectors, or microphones, that may be resident in a housing or a plurality of housings that is/are worn on the chest as shown in FIG. 4A and discussed below. The speakers disclosed herein may be configured to create acoustic resonances in an animal body (e.g., a human lung or trapped air pockets within a human lung), preferably with reduced, or minimal, distortion that may be caused when the sound travels through the body. The devices disclosed herein may be configured to communicatively couple to an external processing device such as a smart phone or computer via, for example, a wired and/or wireless communication protocol and/or via a communication network like the Internet or a Wi-Fi network. The external processing device may have a software program/application stored thereon configured to, for example, receive detected sound from one or microphones, analyze the detected sound for the presence of resonant frequencies, and/or determine a lung resonance signature (LRS) for a wearer's body, lung, or a portion thereof.

When a wearer is being monitored over time, the software program may be further configured to compare measurements taken at different times (e.g., hours, days, weeks, or months apart) to determine changes to the characteristics of the wearer's body, lung, or a portion thereof. This may be useful in monitoring wearer's disease progression over time in order to, for example, determine how a wearer's behavior and/or treatment may be impacting their condition and/or determine when a wearer's condition may be declining and an intervention (e.g., supplemental oxygen, medication, etc.) may be necessary to, for example, prevent further decline, make the wearer more comfortable and/or otherwise improve the wearer's quality of life. In some embodiments, the systems, devices, and methods disclosed herein may be used to reliably monitor lung function and detect lung function deterioration early on in the deterioration cycle so that less invasive and expensive treatments may be administered to reverse, or slow, the deterioration thereby, for example, improving wearer outcomes, slowing lung deterioration, and avoiding mortality events. For example, during COPD exacerbations, air trapping in a wearer's lung(s) is known to increase via, for example, a change in the size and/or volume of one or more trapped air pockets and/or an increase in a number of trapped air pockets within a lung, which may, in turn, change the wearer's LRS. Thus, by continuously and/or periodically monitoring the wearer's LRS, the systems, devices, and methods disclosed herein can be configured to detect changes in lung function and, in the event of deterioration, alert the wearer and/or a caregiver (e.g., clinician, nurse, etc.) of the patient in time for appropriate medical intervention preferably before the wearer has to be admitted or readmitted to the hospital or invasive treatment has to be administered. Additionally, or alternatively, by monitoring real-time and/or long-term trends in lung performance, the systems, devices, and methods disclosed herein may also assist wearers, caregivers, and health providers identify disease triggers, plan daily activities, and assess the efficacy of medications and other treatments. In some cases, this real-time and/or long-term monitoring of lung performance or other physiological systems may utilize local and/or cloud-based processing and/or storage of acoustic data detected by one or more detectors/microphones.

In some embodiments, the LRS may be combined with other aspects and/or characteristics of a wearer to develop a physiological profile for the wearer. Exemplary wearer characteristics include, but are not limited to, age, gender, diagnosis, disease state, weight, resting heart rate, blood pressure, hemoglobin oxygen saturation levels, endurance levels, treatments administered, treatment compliance rates for the wearer, known allergies for the wearers, and known lung function deterioration function triggers (e.g., air pollution, stress, etc.) for the wearer in particular and/or wearers with a diagnosis similar to the particular wearer.

Figure 2A:
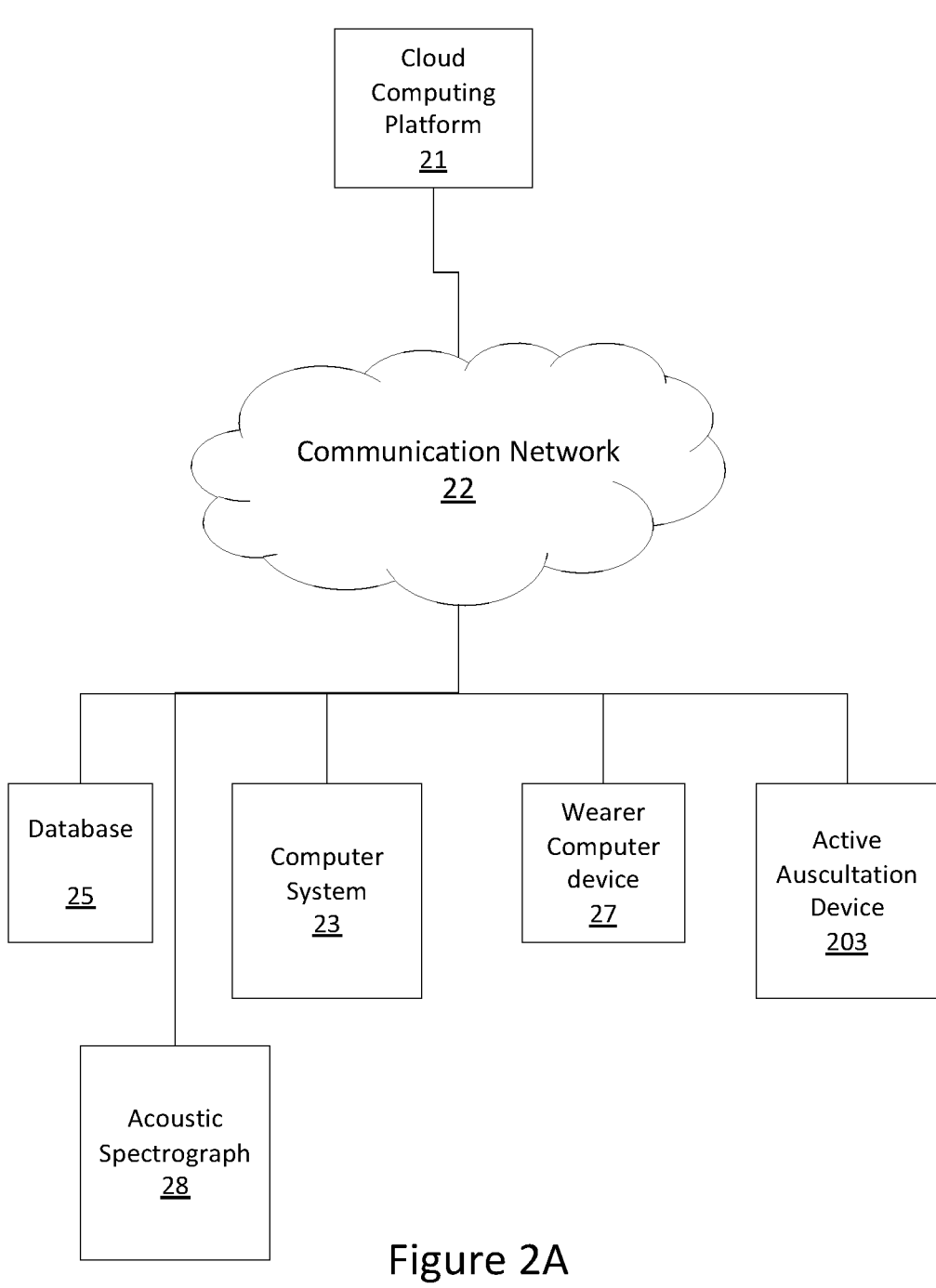
FIG. 2A is a block diagram showing exemplary components of a networked system in which computer readable instructions instantiating the methods of the present invention may be stored and executed, consistent with some embodiments of the present invention.

FIG. 2A provides a system diagram of an exemplary system 201 that may be used to perform one or more methods disclosed herein. System 201 includes a cloud computing platform 21, a communication network 22, a computer system 23, an active auscultation device 203, a database 25, a wearer computer device 27, and an acoustic spectrograph 28. It will be appreciated that in some embodiments, system 201 may not include all the components shown in FIG. 2A and/or may include additional components other than those shown in FIG. 2A.

In some instances, communication network 22 is the Internet. Additionally, or alternatively, communication network 22 may be a private network within, for example, an institution (e.g., a hospital or system of medical treatment facilities). The components of system 201 may be coupled together via wired and/or wireless communication links. In some instances, wireless communication of one or more components of system 201 may be enabled using short-range wireless communication protocols designed to communicate over relatively short distances (e.g., BLU-ETOOTH®, near field communication (NFC), radio-frequency identification (RFID), and Wi-Fi) with, for example, a computer or personal electronic device (e.g., tablet computer or smart phone) as described below. Often times, communication between components of system 201 may be compliant with one or more security protocols, laws, and/or policies that may protect sensitive personally identifying and/or healthcare data.

Cloud computing platform 21 may be any cloud computing platform 21 configured to receive and/or store information and/or execute one or more of the processes disclosed herein. Exemplary cloud computing platforms include, but are not limited to, Amazon Web Service (AWS), Rackspace, and Microsoft Azure.

Computer system 23, active auscultation device 203, and/or wearer computer device 27 may be configured to act as a communication terminal to cloud computing platform 21 via, for example, communication network 22 and may communicate (directly and/or indirectly) measurements taken and/or data collected by active auscultation device 203 to cloud computing platform 21. Exemplary computer systems 23 and/or wearer computer devices 27 include desktop and laptop computers, servers, tablet computers, personal electronic devices, mobile devices (e.g., smart phones), and the like. In some instances, computer system 23 may include a display device.

Computer system 23 active auscultation device 203, and/or wearer computer device 27 may be communicatively coupled to database 25, which may be configured to store sets of instructions for computer system 23 and/or cloud computing platform 21. Acoustic spectrograph 28 may be a spectrograph that may be able to analyze an acoustic signal, or a set of acoustic signals, and generate a two-dimensional or three-dimensional of, for example, time, frequency, and/or intensity of the acoustic signal, or a set of acoustic signals, to generate a spectrograph such as the spectrograph images shown in FIGS. 5A-5D and/or 6A-6D.

One or more components (e.g., database 25, computer system 23, wearer computer device 27, active auscultation device 203, and/or cloud computing platform 21) may store machine-readable instructions and/or receive machine-readable instructions via, for example, communication network 22, that when executed by a processor (e.g., a processor of computer system 23, wearer computer device 27, active auscultation device 203, and/or cloud computing platform 21) may perform one or more methods, processes, and/or method steps and/or generate measurement data disclosed herein.

Figure 2B:
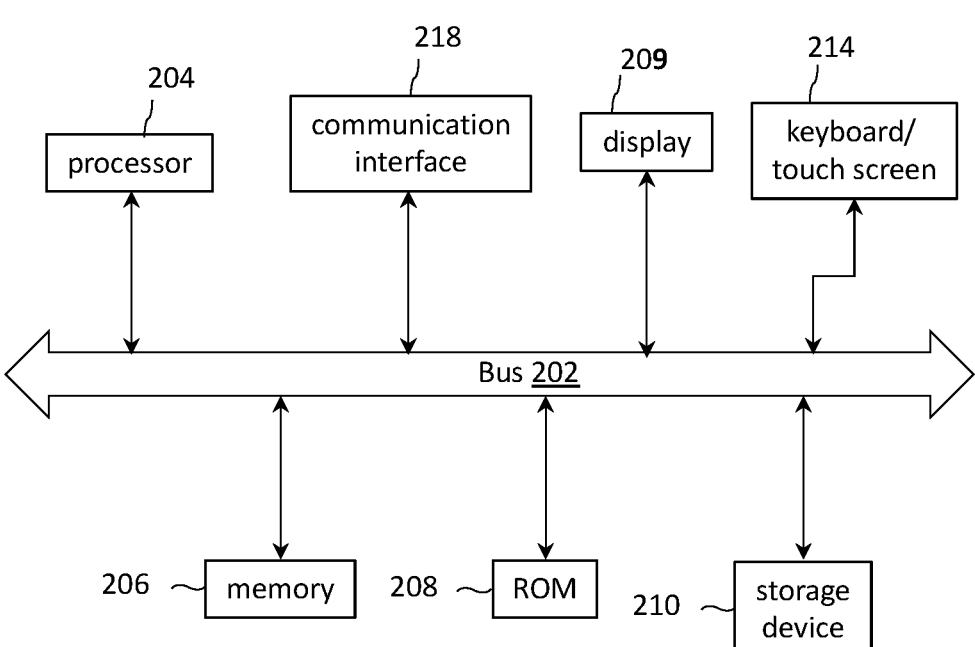
FIG. 2B is a block diagram showing exemplary components of a system in which computer readable instructions instantiating the methods of the present invention may be stored and executed, consistent with some embodiments of the present invention.

FIG. 2B provides an example of a system 202 that may be representative of any of the computing systems (e.g., cloud computing platform 21, computer system 23, wearer computer device 27, active auscultation device 203, and/or audio spectrograph 28) discussed herein. Examples of system 202 may include a smartphone, a desktop computer, a tablet computer, a laptop, an embedded system, etc. Note, not all of the various computer systems disclosed herein have all of the features of system 202. For example, certain ones of the computer systems discussed above may not include a display inasmuch as the display function may be provided by a client computer communicatively coupled to the computer system or a display function may be unnecessary. Such details are not critical to the present invention.

System 202 includes a bus 202 or other communication mechanism for communicating information, and a processor 204 coupled with the bus 202 for processing information. Computer system 202 also includes a main memory 206, such as a random-access memory (RAM) or other dynamic storage device, coupled to the bus 202 for receiving and/or storing information and instructions to be executed by processor 204. Main memory 206 also may be used for storing temporary variables or other intermediate information during execution of instructions to be executed by processor 204. Computer system 202 further includes a read only memory (ROM) 208 or other static storage device coupled to the bus 202 for storing static information and instructions for the processor 204. A storage device 210, for example a hard disk, flash memory-based storage medium, or other storage medium from which processor 204 can read, is provided and coupled to the bus 202 for storing information and instructions (e.g., operating systems, applications programs and the like).

Computer system 202 may be coupled via the bus 202 to a display 209, such as a flat panel display, for displaying information to a computer user. An input device 214, such as a keyboard including alphanumeric and other keys, mouse, track pad, and/or a touch screen, may be coupled to the bus 202 for communicating information, sets of instructions, command selections, directional information, gestures, and controlling cursor movement of/input by the user to the processor 204.

The processes referred to herein may be implemented by processor 204 executing appropriate sequences of computer-readable instructions contained in main memory 206. Such instructions may be read into main memory 206 from another computer-readable medium, such as storage device 210, and execution of the sequences of instructions contained in the main memory 206 causes the processor 204 to perform the associated actions. In alternative embodiments, hard-wired circuitry or firmware-controlled processing units may be used in place of, or in combination with, processor 204 and its associated computer software instructions to implement the invention. The computer-readable instructions may be rendered in any computer language.

In general, all of the process descriptions provided herein are meant to encompass any series of logical steps performed in a sequence to accomplish a given purpose, which is the hallmark of any computer-executable application. Unless specifically stated otherwise, it should be appreciated that throughout the description of the present invention, use of terms such as "processing", "computing", "calculating", "determining", "displaying", "receiving", "transmitting" or the like, refer to the action and processes of an appropriately programmed computer system, such as computer system 202 or similar electronic computing device, that manipulates and transforms data represented as physical (electronic) quantities within its registers and memories into other data similarly represented as physical quantities within its memories or registers or other such information storage, transmission or display devices.

Computer system 202 also includes a communication interface 218 coupled to the bus 202. Communication interface 218 may provide a two-way data communication channel with a computer network, which provides connectivity to and among the various computer systems discussed above. For example, communication interface 218 may be a local area network (LAN) card to provide a data communication connection to a compatible LAN, which itself is communicatively coupled to the Internet through one or more Internet service provider networks. The precise details of such communication paths are not critical to the present invention. What is important is that computer system 202 can send and receive messages and data through the communication interface 218 and in that way communicate with hosts accessible via the Internet. It is noted that the components of system 202 may be located in a single device or located in a plurality of physically and/or geographically distributed devices.

Figure 2C:
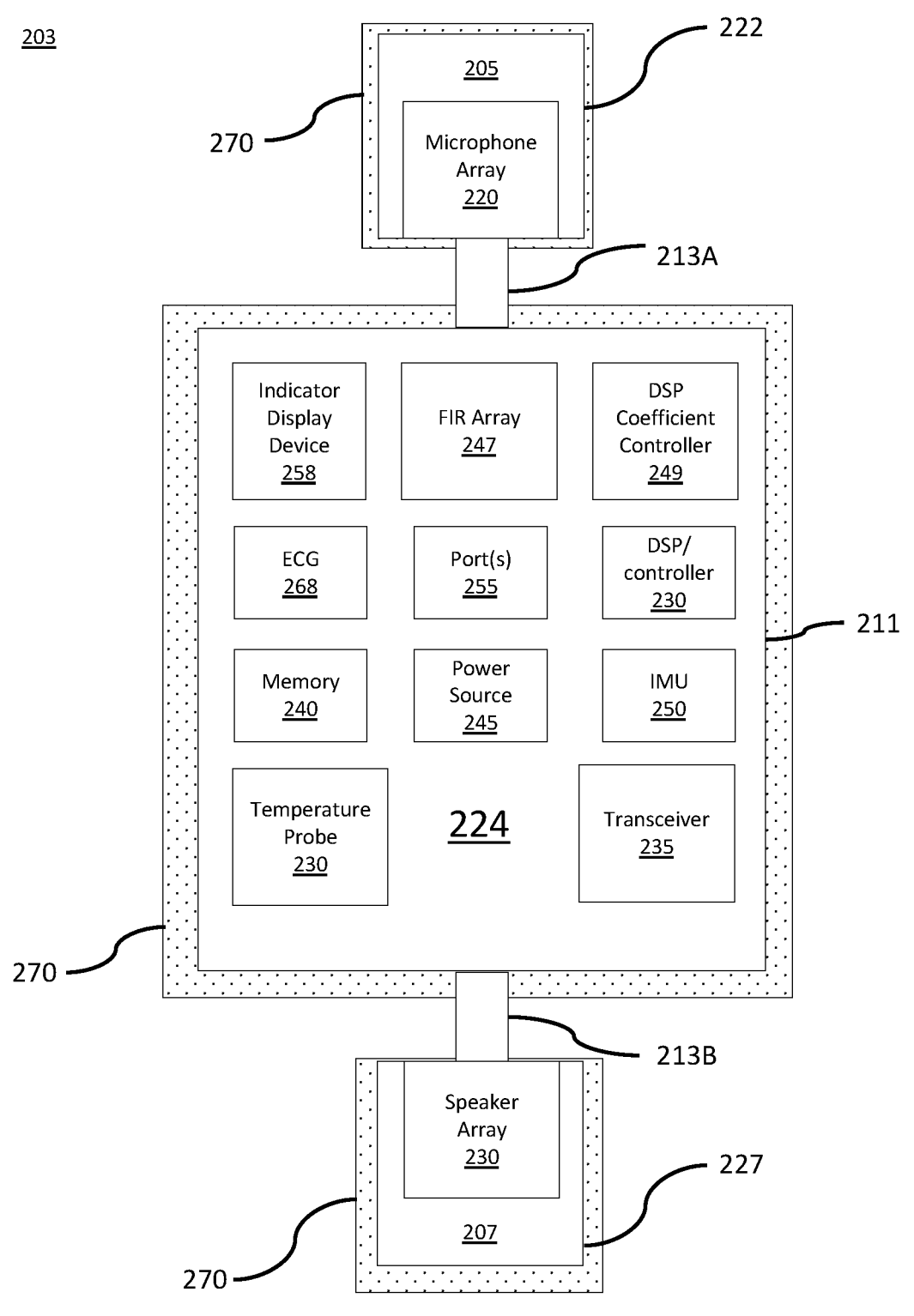
FIG. 2C is a block diagram showing exemplary components of an exemplary active auscultation device, consistent with some embodiments of the present invention.

FIG. 2C is a block diagram of an exemplary set of components 203 that may be included in one or more of the active auscultation devices disclosed herein. Set of components 203 may also be referred to herein as active auscultation device 203. The set of components that make up active auscultation device 203 include a set of main body components 224 housed in a main body housing 211, a set of microphone wing components 205 housed in a microphone wing housing 222, and a set of speaker wing components 207 housed in a speaker wing housing 227.

Set of microphone wing components 205 and microphone wing housing 222 may be mechanically, communicatively, and/or electrically coupled to set of main body components 224 and/or main body housing 211 via a first flexible coupling 213A that may physically and/or mechanically attach to both microphone wing housing 205 and main body housing 211 and electrically and/or communicatively couple one or more components of set of microphone wing components 205 to set of main body components 224 via, for example, wire leads embedded in first flexible coupling 213A. Set of speaker wing components 207 and speaker wing housing 227 may be mechanically, communicatively, and/or electrically coupled to set of main body components 224 and/or main body housing 211 via a second flexible coupling 213B that may physically and/or mechanically attach to both speaker wing housing 207 and main body housing 211 and electrically and/or communicatively couple one or more components of set of speaker wing components 207 to set of main body components 224 via, for example, wire leads embedded in second flexible coupling 213B. First and/or second flexible couplings 213A and 213B may be configured to allow first and/or speaker wing housing 227 and 227 to articulate in one or more directions relative to main body housing 211 in order to, for example, allow for bending an overall shape of active auscultation device 203 so that it may adhere to a curved or bumpy portion (e.g., chest or side) of a wearer's body. First and/or second flexible couplings 213A and 213B may comprise any flexible material including, but not limited to, cords, mesh, plastic, and/or vinyl cable covering. In some embodiments, first and/or second flexible couplings 213A and 213B may be expandable via, for example, a spool resident in microphone wing housing 222, speaker wing housing 227, and/or main body housing 211 and/or an expandable material (e.g., a spring or expandable foam).

Active auscultation device 203 may be configured to be wearable by a wearer for a short (e.g., 5-20 minutes) and/or long (days or weeks) duration of time. An underside of active auscultation device 203 may include attachment mechanism (e.g., an adhesive or flexible material) or mechanism component (e.g., an attachment mechanism configured to cooperate with, for example, a strap, sleeve, harness, and/or garment) by which to attach to a wearer's skin as shown in, for example, FIG. 2B, which is discussed below. At times, the attachment mechanism may be an acoustic dampener and/or isolator configured to isolate components of active auscultation device 203 from externally generated sound. Exemplary dimensions for active auscultation device 203 are 1-5 cm wide, 2-20 cm long, and 0.3-2 cm high. Set of microphone wing components 205 and set of speaker wing components 207 may be mechanically, electrically, and/or communicatively coupled to set of main body components 224. In some embodiments, one or more portions of active auscultation device 203 may be removable and/or interchangeable with a similar or different component.

In some instances, active auscultation device may further comprise an on/off button (not shown), an indicator display device 258 that may be, for example, a light source. The light source may be a light emitting diode (LED) that emits light in one or more colors and, in some cases, light of varying colors or patterns may correspond to different information (e.g., a red light may indicate that memory 240 is almost full or that battery 245 is nearly discharged and a green light may indicate that all components of active auscultation device 203 are functioning properly) being provided by active auscultation device 203 to an external observer. The on/off button may be configured to turn on, turn off, or trigger a measurement by active auscultation device 203.

In some embodiments, active auscultation device 203 may be configured to be affixed to a wearer's chest (e.g., below the pectoral muscle or over the lung) or back. In some cases, a mechanical coupling between set of main body housing 211, microphone wing housing 222 and/or speaker wing housing 227 may be flexible so that microphone wing housing 222 and/or speaker wing housing 227 may articulate relative to main body housing 211 to, example, accommodate a curvature of a wearer's torso and/or movement of a wearer's torso while breathing and accomplish a skin-tight fit that inhibits intrusion of noise into the active auscultation device from the environment and leaking of acoustic signals from the active auscultation device into the environment.

In an alternate embodiment, microphones and speakers may be incorporated into the main body and the wings may not be a component of the active auscultation device. Additionally, or alternatively, one or more wings, or components of an active auscultation device 203 may not be physically coupled to the main body via, for example, first and/or second flexible coupling 213A and/or 213B. In these embodiments, the component or housing (e.g., microphone wing housing 222 and/or speaker wing housing 227) may not physically attached to the main body housing but may be communicatively coupled to one or more components of the set of main body components 224 via, for example, a near-field communication protocol (e.g., BLUETOOTH™). In some cases, one or more components of an active auscultation device 203 may be positioned around the wearer's body while not being physically coupled to main body housing 211 in order to, for example, facilitate projecting an acoustic signal into/detecting acoustic signals from different regions of the wearer's body and/or projecting acoustic signals at different angles into the wearer's body. In some cases, analysis of detected acoustic signals may incorporate location analysis (e.g., triangulation) based on where a component projecting the acoustic signal and/or detecting the acoustic signal is positioned on the wearer's body.

Set of main body components 224 may comprise a memory unit 240, a power source 245 (electrically coupled to some, or all, of the components of active auscultation device 203), a digital signal processor (DSP) 230, a transceiver 235, which is some cases may be a BLUETOOTH™ low energy/microcontroller unit (BLE/MCU), a port 255, an indicator display device 258, an electrocardiogram (ECG) device 268, FIG array 247, a DSP coefficient controller 249, an inertial movement unit (IMU) 250, and a temperature probe 225 housed within housing 211 as shown in FIG. 2B. Set of microphone wing components 205 may include a microphone array 220 of one or more microphones housed within a microphone wing housing 222. Set of speaker wing components 207 may include a speaker array that includes one or more speakers. In some embodiments, active auscultation device 203 may include a sound dampening material (not shown) that may be configured to, for example, absorb sound from one or more speakers of speaker array 230 so that it is not heard by the wearer. Additionally, or alternatively, the sound dampening material may be configured to isolate the microphone(s) of microphone array 220 from external noise (e.g., ambient noise and/or noise generated by the wearer via, for example, breathing and/or coughing) and/or acoustically separate a first microphone of microphone array 220 from a second microphone of microphone array 220.

In some embodiments, all, or a portion of, active auscultation device 203, microphone wing housing 222, speaker wing housing 227, first flexible coupling 213A, and/or second flexible coupling 213B may be water resistant or water proof so that they are, for example, impervious to perspiration of the wearer and/or water that may be encountered when, for example, active auscultation device 203 is being worn (e.g., when wearer takes a shower) and/or when active auscultation device 203 is being washed or cleaned. In some embodiments, set of main body components 224 may be removably attached to active auscultation device 203 so that, for example, set of main body components 224 and/or main body housing 211 may be removed from active auscultation device 203 in order to, for example, recharge power source 245 and/or be interchanged with another set of main body components 224 when, for example, replacing set of main body components 224. In some embodiments, set of main body components 224 may be temporarily removed prior to when a wearer is exposed to water when, for example, showering or swimming. An example of a replaceable/interchangeable main body component, in the form of an exemplary removable main body housing 330, is shown in FIG. 3E and discussed below.

Speaker(s) included in speaker array 230 may be configured to emit an acoustic energy and/or an acoustic signal (sometimes referred to herein as an emitted acoustic signal) when activated by, for example, DSP/controller 230. The acoustic energy/signal may be of, for example, a particular frequency or set of frequencies; typically, within a range of 100 Hz to 25 KHz. In some cases, the frequency of the acoustic energy may change over time responsively to, for example, the wearer's interactions with the acoustic energy/signal and any resonant frequencies that may be detected. The set of frequencies emitted by a speaker of speaker array 230 may be intentionally, randomly, and/or pseudo randomly selected. At times, the acoustic signal may be in the ultrasound range. In some embodiments, the set of frequencies emitted by a speaker of speaker array 230 may be responsive to a characteristic of a particular wearer. For example, if it is known that the wearer has demonstrated resonance at one or more particular frequencies (or bands of frequencies) in the past, a speaker of speaker array 230 may be configured via, for example, an instruction and/or signal from DSP/controller 230 and/or an external device in communication with active auscultation device 203 (e.g., computer system 23 and/or wearer computer device 27) to emit an acoustic signal at these frequencies when taking further, or subsequent, measurements of the wearer. In some embodiments, one or more of the speakers of speaker array 230 may be a single channel speaker. Additionally, or alternatively, one or more of the speakers of speaker array 230 may be configured to emit sound on a plurality (2, 3, 4, etc.) of channels. An exemplary acoustic power range for a speaker of speaker array 230 is 80-110 dBA for white noise stimuli at 20 cm from speaker measured on axis.

One or more of the microphones of microphone array 220 may be configured to detect acoustic energy emanating from the wearer's body responsively to sound emitted into the wearer's body by one or more of the speakers of speaker array 230 and provide the detected acoustic energy (also referred to herein as a "detected acoustic signal") to DSP/controller 230 and/or transceiver 235 for communication to an external device (e.g., one or more of the components of system 201 and/or 202). In some cases, the detected acoustic signal may be associated with a microphone identifier so that, for example, DSP/controller 230 can determine which microphone of microphone array 220 the detected acoustic signal came from. This identifier may be used to, for example, determine a direction of the detected acoustic signal came from so that, for example, a location of a resonating portion of the wearer's body (e.g., a pocket of trapped air) may be located. In some embodiments, DSP/controller 230 may determine which microphone of microphone array 220 the detected acoustic signal came from by analyzing the content of the detected acoustic signal. This analysis may be used to determine, for example, a frequency content, a start/stop time of the detected acoustic signal, and/or other characteristics (e.g., intensity, noise, etc.) of a detected acoustic signal.

In some exemplary embodiment wherein microphone array 220 includes two microphones, a first microphone and/or a second microphone may have a range for detecting an acoustic signal of, for example, 500 Hz to 20 kHz, with +/−3 dB frequency response on range 5 KHz to 15 KHz. At times, the first microphone may be directed toward a wearer and the second microphone may directed away from the wearer in order to, for example, capture ambient noise that may be later removed from the sound detected by the first microphone via, for example, application of a noise cancelling algorithm to the acoustic signal detected by the first microphone. The noise cancelling algorithm may be informed and/or adjusted responsively to one or more characteristics (e.g., frequency and/or intensity) the ambient noise detected by the second microphone.

Temperature probe 225 may be configured to measure a temperature of the active auscultation device 203 and/or the wearer. In some cases, when a temperature of the active auscultation device 203 is above a threshold, a warning notification may be sent to a wearer and/or active auscultation device 203 may power down in order to prevent burning of, or discomfort to, the wearer. Additionally, or alternatively, when a temperature of the wearer is above a threshold (as may indicate that the wearer has a fever), active auscultation device 203 may be activated to take a high- and/or low-resolution measurement. In some embodiments, temperature probe 225 may be configured to measure a temperature of the wearer at periodic (e.g., every minute, every 5 minutes, every hour) and/or as-needed intervals responsively to, for example, an instruction from DSP/controller 230 that, in some instances, may correspond to a measurement taken by another component of active auscultation device 203.

In some embodiments, temperature measurements and/or changes in temperature measurements over time may trigger one or more operations by active auscultation device 203 such as the taking of a quick and/or low resolution acoustic measurement, the taking of a slow and/or high resolution acoustic measurement, taking an ECG measurement, and/or activating one or more components of active auscultation device 203 to take additional measurements and/or communicate with an external computing device. Exemplary communications include, but are not limited to, alarm conditions, measurement values, and/or system malfunction notifications (in the event that the active auscultation device 203 (not the patient) is too hot). Exemplary measurements that may trigger an action by active auscultation device 203 include, but are not limited to, changes in the wearer's body temperature over time (e.g., an increase of 1 degree in less than 1 hour) and/or if a temperature change is measured and there is no corresponding data from, for example, IMU 250 to indicate a change in activity level (e.g., exercise).

Temperature measurements may be recorded on, for example, memory 240 and in some instances may be time-stamped and/or correlated with detected acoustic signals. At times, temperature probe 225 may be configured to draw a relatively small amount of power from power source 245 so that it may, for example, continuously monitor a temperature of the wearer without adversely impacting battery life in a substantial way. For example, in some embodiments, transceiver 235 may be configured to become active, or wake up, periodically and instruct temperature sensor 225 to measure the temperature and query IMU 250 to determine whether IMU 250 has recorded any new motion of the wearer. In this way, active auscultation device 203 may be configured to operate in a low-power, or sleeping, state that draws very low current from power source 245 for a duration of time and may be configured to power on, or wake up at periodic intervals (e.g., every second, 30 seconds, minute, or hour) to measure the wearer's temperature and transceiver 235 and/or DSP/controller 230 may determine whether or not to wake one or more additional components of active auscultation device 203 to take one or more additional measurements and/or return to a resting/sleeping state responsively to the temperature measurement.

One or more port(s) 255 may be configured as a power port by which power source 245 may be charged. Additionally, or alternatively, port 255 may be configured as a communication port by which active auscultation device 203, or components resident therein, may communicate with one or more external devices (e.g., a computer or processor). Exemplary ports 255 include, but are not limited to, a mini USB, micro USB, USB-C, or other data/power mechanism. Power source 245 may be configured to provide power to one or more components of active auscultation device 203 and may be a rechargeable or not rechargeable (e.g., disposable) battery and/or port configured to draw energy from an electrical main. In some embodiments power for active auscultation device 203 may be provided directly via an electrical connection to port 255 from, for example, an external battery pack (not shown) or wall outlet coupled to main line electrical power. Additionally, or alternatively, power for active auscultation device 203 may be provided directly via an electrical induction coil (not shown) positioned within and/or on a housing for active auscultation device 203 that is configured to cooperate with an electrical induction power source (e.g., a magnet) external to the housing to, for example, charge a battery within the housing.

Indicator display device 258 may be configured to provide one or more indications regarding an operation or status of active auscultation device 203 such as battery power level, storage capacity, when active auscultation device 203 is communicating with an external device, and/or experiencing an error condition. Exemplary indicator display devices 258 include, but are not limited to, light emitting diodes (LEDs), touch screen displays, and LCD display screens.

Memory 240 may be configured to receive, and store detected acoustic signal(s) emanating from the wearer's skin that are detected by one or more microphone(s) of microphone array 220 and/or received from DSP/controller 230. In some embodiments, memory unit 240 may be further configured to store instructions regarding the operation of one or more components of active auscultation device 203 such as DSP/controller 230, a speaker of speaker array 230, temperature probe 225, IMU 250, transceiver 235, and/or indictor display device 258. In some embodiments, the instructions may be received via, for example, port 255 and/or transceiver 235. In some embodiments, DSP/controller 230 may be a microcontroller configured to control the operation of one or more components of active auscultation device 203. In some embodiments, DSP/controller 230 may include and/or be in communication with a timer module, so that after a specified amount of time has passed, DSP/controller 230 may activate active auscultation device 203.

Transceiver 235 may be a communication module such as a Bluetooth low energy communication module. In some embodiments, active auscultation device 203 may be configured to be in electronic communication with an external electronic device (e.g., computer system 23 and/or wearer computer device 27) that may be running a software application configured to communicate with active auscultation device 203 and provide one or more instructions thereto and/or receive information from active auscultation device 203. In some embodiments, this communication may allow the wearer and/or a user (e.g., doctor or caretaker) to operate active auscultation device 203 remotely, or semi-remotely, transfer data from active auscultation device 203 to the external electronic device and/or transfer instructions and other data to active auscultation device 203. In some embodiments, the external electronic device may then transfer the data to a third party, such as a medical practitioner, a company working with the medical practitioner and/or to a cloud computing environment, and/or cloud computing platform 21. In some embodiments, the software and/or firmware used by active auscultation device 203 may be updated and/or modified via instructions received by transceiver 235. At times, transceiver 235 may be configured to communicate, for example, battery charge level, diagnostic information, and/or one or more measurements taken by active auscultation device 203 to, for example, an external computing device (e.g., a wearer's smart phone or other computing device running software application as described herein).

In some embodiments, active auscultation device 203 may communicate with the external electronic device to transmit data regarding a status (e.g., battery level and other diagnostic information such as the number of measurements currently in the memory) of active auscultation device 203. In some embodiments, active auscultation device 203 may be configured to continuously transmit data for small periods of time.

IMU 250 is an inertial movement unit, or accelerometer, configured to detect movement of the wearer as may occur with the wearer is breathing and/or ambulatory. In some embodiments, IMU 250 may be configured to activate/deactivate active auscultation device 203 when movement is detected and/or provide an indication to DSP/controller 230 that may cause DSP/controller 230 to activate active auscultation device 203. In some embodiments, IMU 250 may be configured to activate active auscultation device 203 when movement exceeds a predetermined threshold as measured by the IMU. In some embodiments, IMU 250 and/or DSP/controller 230 in communication with IMU 250 may be configured to recognize a movement pattern of the wearer such as walking and/or coughing and active auscultation device 203 may be activated and/or deactivated responsively to a detected pattern. Movement and/or activity of a wearer may be measured periodically (e.g., 1, 5, or 10 minutes) and/or as needed (e.g., a movement is detected and then wearer is monitored for movement until no or reduced movement is detected) and may be stored for download from active auscultation device 203. Additionally, or alternatively, movement and/or activity measurements may be sent to DSP/controller 230, which may analyze the movement and/or activity measurements to determine whether there is a change in movement and/or activity measurement and/or whether a threshold condition is reached (e.g., movement that resembles inhaling and/or exhaling a deep breath) and, if so, such a determination may be used to trigger performance of other operations and/or measurements by active auscultation device 203.

ECG device 268 may be an electrocardiography device that measures the wearer's heart rate and provides the wearer's heart rate to, for example, DSP/controller 230 and/or transceiver 235 for communication to an external processing device. Fluctuations in a wearer's heart rate, as measured by the ECG device 258, may trigger the taking of a high- and/or low-resolution measurements by active auscultation device 203 as, for example, disclosed herein.

In some embodiments, active auscultation device 203 may include one or more finite impulse filters (FIR) shown in FIG. 2C as FIR array 247 that may be physically, electronically, and/or communicatively coupled to one or more of the microphones of microphone array 220, DSP/controller 230, and/or transceiver 235. For example, in some embodiments, microphone array 220 has a first, second, and third microphone and FIR array 247 may have a corresponding first FIR physically, electronically, and/or communicatively coupled to the first microphone, a second FIR physically, electronically, and/or communicatively coupled to the second microphone, and a third FIR physically, electronically, and/or communicatively coupled to the third microphone. In these embodiments, the first microphone may communicate a first acoustic signal it detects to the first FIR; the second microphone 220B may communicate a second acoustic signal it detects to the second FIR 410B; and the third microphone may communicate a third acoustic signal it detects to the third FIR 410C. The first, second, and/or third FIRs may then process the detected signals in, for example, real time for improved audio performance by, for example, mixing one or more of the first, second, and/or third detected signals and/or using finite impulse response analysis and/or finite impulse response filters to process and/or filter the respective first, second, and/or third detected acoustic signals. In some cases, the signals processed by the first, second, and/or third FIRs may be communicated to DSP/controller 230 for further processing and/or optimization by application of, for example, one or more coefficients generated by a DSP coefficient controller 249. An optimized audio signal may then be communicated by DSP/controller 230 to an external component and/or processing device via, for example, transceiver 235 and/or port 255.

In some embodiments, one or more of the FIRs of FIR array 247 may have a plurality of coefficients (e.g., 10-65) per FIR and/or microphone coupled to an FIR that may be received from, for example, DSP coefficient controller 249 and/or DSP/controller 230. The coefficients may be applied to a detected acoustic signal in order to, for example, improve signal quality and/or accuracy of measurement and/or analysis results determined using the detected acoustic signals. In some cases, the coefficients may be established and/or adjusted responsively to one or more factors that may impact, for example, measurements taken by active auscultation devices 203 and/or the quality of those measurements. At times, these adjustments may be done in real time (or close to real time) as detected acoustic signals are received, which may allow for the adjustment of FIR coefficients and/or processing in synch with the detected acoustic signals, which may, for example, improve signal quality (e.g., reduce noise, amplify desired portions of the signal etc.) and/or intensity. In some cases, adjustment of one or more of the coefficients may include execution of one or more calibration processes that may be performed to, for example, maximize the intensity of the signal the microphones are detecting and/or providing to their respective FIR of FIR array 247.

At times, one or more coefficients for FIRs of FIR array 247 may be optimized to, for example, maximize the energy and/or power of the detected acoustic signal(s). This optimization may be done by, for example, determining whether the sum and/or mix of detected acoustic signals communicated to and/or received by DSP/controller 230 has sufficient energy (e.g., intensity, power, etc.) and/or clarity (e.g., signal-to-noise ratio (SNR)) and, if not, determining how to amplify and/or reduce noise within the detected acoustic signals. By optimizing for maximum energy of the detected acoustic signals among the FIRs of FIR array 247, the coefficient(s) of each FIR may be adjusted and/or calibrated to, for example, create an evenly (or nearly evenly) powerful signal across different microphones by adjusting the amplification across the array of microphones and/or detected acoustic signals. For example, there may be one FIR coefficient per microphone that may adjust the power/intensity/volume of a particular detected acoustic signal and/or frequency across multiple microphones so each detected acoustic signal from each microphone may be accorded the same (or similar) weight in subsequent calculations.

In some cases, a coefficient for a FIR may account for timing discrepancies in the receipt of a detected acoustic signal that may be caused by, for example, a location of different microphones relative to target tissue (e.g., lung or pockets of trapped air within a lung). For example, if a first microphone within microphone array 220 is 4 cm closer to an emitted acoustic signal source (e.g., a speaker of speaker array 230) than a fourth microphone of microphone array 220 then, the FIR corresponding to the fourth microphone may add more volume on the coefficient for the fourth FIR 440D relative to the volume for the first microphone, which may act to amplify the delayed signal received by the fourth microphone 220D and/or may make the acoustic signal detected by the fourth microphone 220D overlap itself (which may increase intensity/power of the signal).

In some embodiments, one or more microphones of microphone array 220 may be configured so that when active auscultation device 203 is worn, the one or more microphones point away from the wearer's chest in order to capture ambient noise in an environment and a subtracting coefficient (e.g., −1) may be applied to the detected acoustic signal from this microphone so that, for example, the ambient noise is subtracted from the detected acoustic signals of the remaining microphone(s) of the array.

Optionally, a surface of one or more of microphone wing housing 222, speaker wing housing 227, and/or main body housing 211 may have an adhesive and/or sound isolating material 270 affixed thereto. In some embodiments, adhesive and/or sound isolating material 270 may be a substrate for the components of active auscultation device 203 and/or a lower surface of microphone wing housing 222, speaker wing housing 227, and/or main body housing 211. Adhesive and/or sound isolating material 270 may be configured to adhere to a wearer's skin for a period of time (e.g., 30 minutes-4 weeks) and, in some cases, may be waterproof. Additionally, or alternatively, adhesive and/or sound isolating material 270 may isolate components of active auscultation device 203 from external acoustic and/or signal noise that may be generated by something other than a speaker of speaker array 230 so that the microphones of microphone array 220 are less likely to detect background noise. Exemplary materials that may be used for adhesive and/or sound isolating material 270 include, but are not limited to, silicon, glue, rubber, and plastic. At times, adhesive and/or sound isolating material 270 may not cover an entirety of a lower portion of microphone wing housing 222, speaker wing housing 227, and/or main body housing 211 so that it does not interfere with the projection of an acoustic signal into the wearer's body or detection of an acoustic signal emanating from the wearer's body. In these embodiments, adhesive and/or sound isolating material 270 may be positioned around and/or encircle a lower exterior portion of microphone wing housing 222, speaker wing housing 227, and/or main body housing 211 in a ring-like manner that does not occlude, for example, microphone array 220 and/or speaker array 230.

Figure 2D:
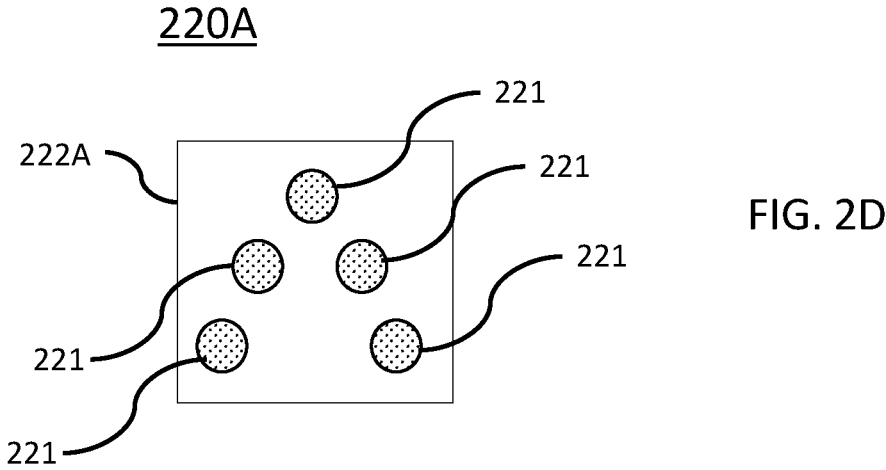
FIG. 2D is a block diagram of a first exemplary microphone array, in accordance with some embodiments of the present invention.
Figure 2E:
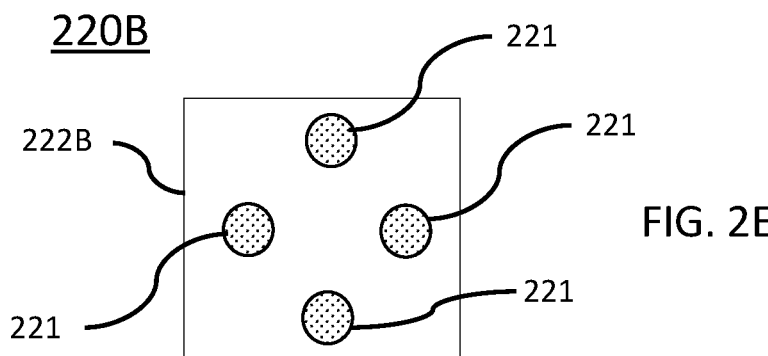
FIG. 2E is a block diagram of a second exemplary microphone array, in accordance with some embodiments of the present invention.
Figure 2F:
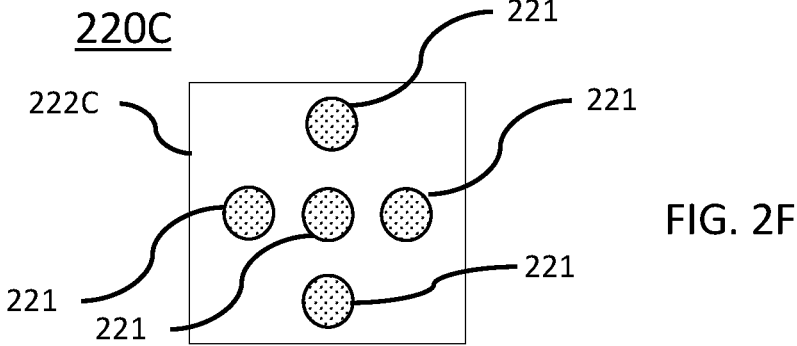
FIG. 2F is a block diagram of a third exemplary microphone array, in accordance with some embodiments of the present invention.
Figure 2G:
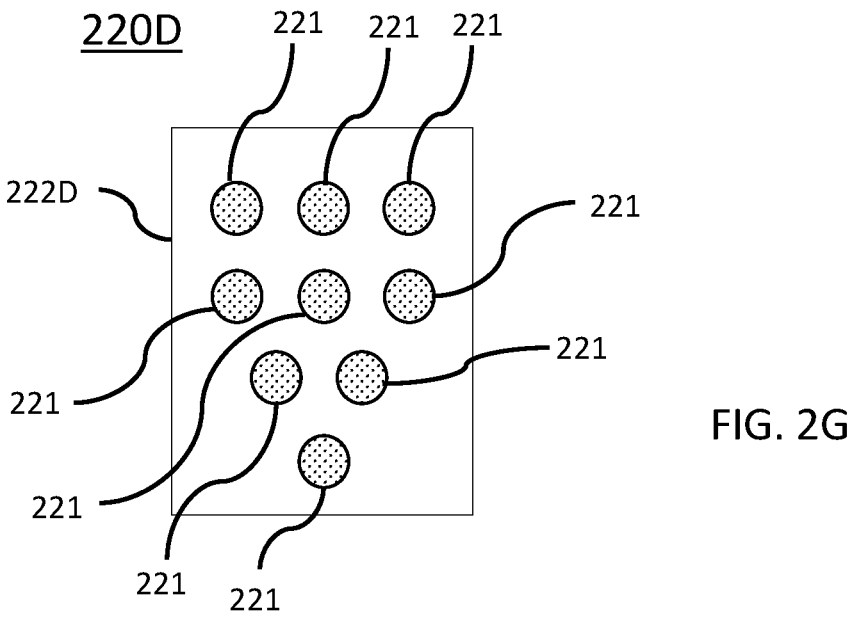
FIG. 2G is a block diagram of a fourth exemplary microphone array, in accordance with some embodiments of the present invention.

In some embodiments, speakers within speaker array 230 and/or microphones within microphone array 220 may be arranged in different positions within microphone wing housing 222 and speaker wing housing 227, examples of which are shown in FIGS. 2D-2J. In particular, FIG. 2D is a diagram of a first microphone array 220A that includes five microphones 221 arranged in triangular formation within a corresponding first microphone wing housing 222A; FIG. 2E is a diagram of a second microphone array 220B that includes four microphones 221 arranged in diamond-like formation within a corresponding second microphone wing housing 222B; FIG. 2F is a diagram of a third microphone array 220C that includes five microphones 221 arranged in cross-like formation within a corresponding third microphone wing housing 222C; and FIG. 2G is a diagram of a fourth microphone array 220D that includes six microphones 221 arranged in rectangular formation and three microphones arranged in a triangular formation within a corresponding fourth microphone wing housing 222D.

The microphones included in one or more of microphone arrays 220A, 220B, 220C, and/or 220D may be pointed or aimed in the same and/or different directions. For example, a microphone 221 in microphone array(s) 220A, 220B, 220C, and/or 220D may be directed away from the wearer and the remainder of the microphones 221 in microphone array(s) 220A, 220B, 220C, and/or 220D may be directed toward the wearer. In some embodiments, all the microphones 211 pointing toward a wearer may be oriented in the same direction (e.g., parallel to a base of microphone wing housing 220) and, in other embodiments, one or more of the microphones 211 pointing toward a wearer may be oriented in the different directions (e.g., 5-85 degrees relative to the base of microphone housing 220). An arrangement and/or orientation of microphones 221 within microphone arrays 220A, 220B, 220C, and/or 220D may be configured to detect sound coming from a particular direction (e.g., toward speaker array 230 and/or away from the speaker array 230) and/or a particular location on the wearer's body. It will be understood that the microphone arrays of FIGS. 2D-2G are exemplary and that a microphone array 220 may include more or fewer (e.g., 1-3 or 10-25) microphones than the arrangements shown in FIGS. 2D-2G.

Figure 2H:
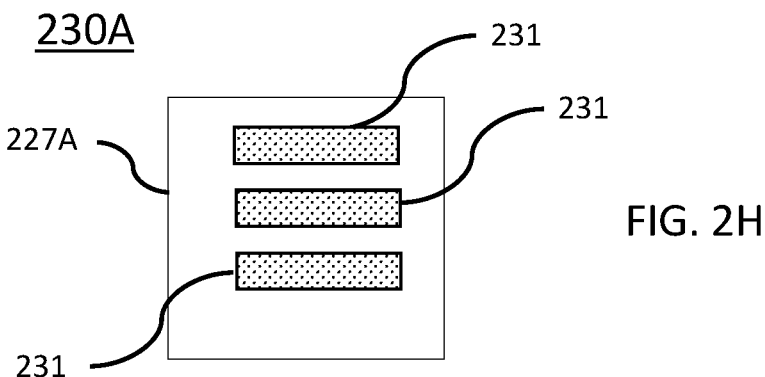
FIG. 2H is a block diagram of a first exemplary speaker array, in accordance with some embodiments of the present invention.
Figure 2I:
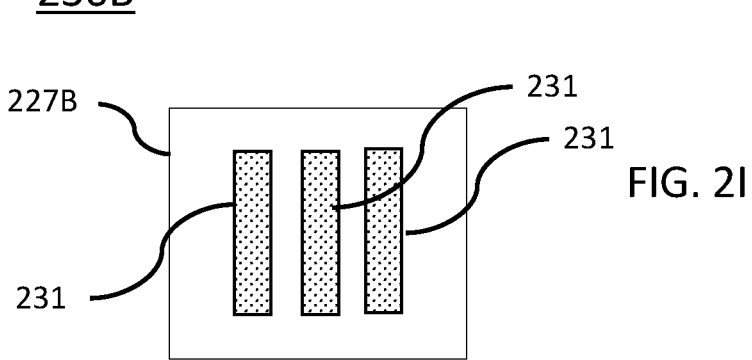
FIG. 2I is a block diagram of a second exemplary speaker array, in accordance with some embodiments of the present invention.
Figure 2J:
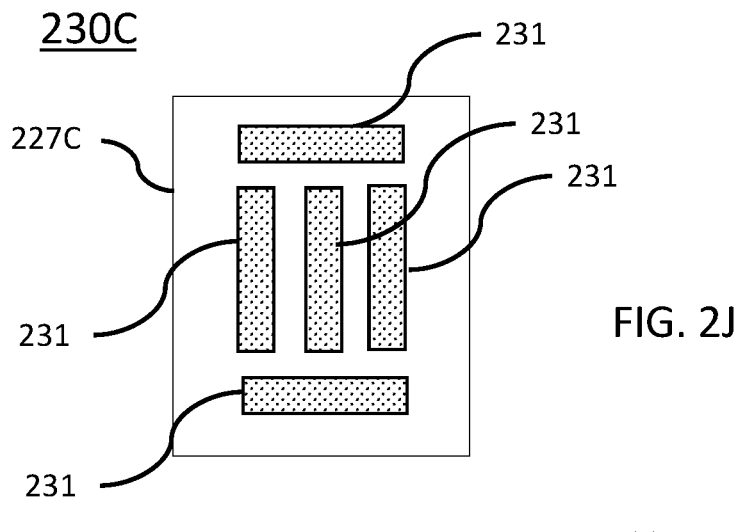
FIG. 2J is a block diagram of a third exemplary speaker array, in accordance with some embodiments of the present invention.

With regard to speaker arrays, FIG. 2H is a diagram of a first speaker array 230A that includes three speakers 231 that are arranged horizontally and are approximately parallel to one another within a first speaker wing housing 230A; FIG. 2I includes three speakers 231 that are arranged vertically and are approximately parallel to one another within a corresponding second speaker wing; and FIG. 2J is a diagram of a third speaker array 230C that includes five speakers 231, with three arranged horizontally and are approximately parallel to one another and two speakers 231 on a top and a bottom (as shown in FIG. 2J) of the three horizontally-arranged speakers 231 within a corresponding third speaker wing housing 227C.

The speakers included in one or more of speaker arrays 230A, 230B, and/or 230C may be pointed or aimed in the same and/or different directions. For example, in some embodiments, all the speakers 231 in a speaker array 230 may point toward a wearer may be oriented in the same direction (e.g., parallel to a base of speaker wing housing 230) and, in other embodiments, one or more of the speakers 231 pointing toward a wearer may be oriented in the different directions (e.g., 5-85 degrees relative to the base of speaker housing 230).

In some cases, activation of a speaker and/or microphone included in a speaker array 230 and/or microphone array 220 may be selective so that not all microphones/speakers in an array are on at the same time. Each speaker in an array may be configured to emit sound at a different time and/or at a different frequency, or set of frequencies (e.g., multiplexing), so that, for example, acoustic energy from different speakers in a speaker array may be distinguished from one another. In some embodiments, acoustic signals may be emitted by one or more of the speakers of speaker array 230 and detected by one or more of the microphones of microphone array 220. The detected acoustic signals from each of the microphones may be analyzed to determine an optimum combination of speaker(s) and/or microphone(s) to use for performing an active auscultation measurement.

In some embodiments, one or more speakers 231 of a speaker array 230 may be configured to emit acoustic energy with a variety of frequencies so as to assess at which frequencies a wearer's body, organ, and/or trapped air pocket(s) resonate and/or determine a set of frequencies to use for subsequently performed active auscultation. In some instances, a set of frequencies for the acoustic signal emitted by one or more of the speakers of speaker array 230 may be randomly and/or pseudo-randomly selected. At times, analysis of detected acoustic signals may then focus on one or more frequencies determined to resonate within the wearer's body and, in some instances, subsequent incident frequencies may be selected based on frequencies determined to resonate within the wearer's body. Instructions for producing an acoustic signal may be received by a speaker 231 and/or speaker array 230 from, for example, DSP/controller 230.

FIG. 3A is a top view and FIG. 3B is a side view of an exemplary active auscultation device 301 that shows set of main body components 224 housed in a rectangularly-shaped main body housing 211, a set of microphone wing components 205 housed in a trapezoid-shaped microphone wing housing 222, and a set of speaker wing components 207 housed in a trapezoid-shaped speaker wing housing 227. Microphone wing housing 222 is electrically, physically, and/or communicatively coupled to main body housing 211 via first flexible coupling 213A and speaker wing housing 227 is electrically, physically, and/or communicatively coupled to main body housing 211 via second flexible coupling 213B. As may be seen in FIG. 3B, active auscultation device 301 adhesive and/or sound isolating material 270 is affixed to a lower (as oriented in FIG. 3B) and skin facing surface of active auscultation device 301.

In addition, FIG. 3B shows second flexible coupling 213B, speaker wing housing 227, and adhesive and/or sound isolating material 270 oriented at a first non-perpendicular angle 215A relative to the right side (as shown in FIG. 3B) of main body housing 211 in order to, for example, accommodate a curvature of a wearer so that each component of active auscultation device 301 may be securely physically coupled to and/or directly abut the wearer's skin. Although second flexible coupling 213B, speaker wing housing 227, and adhesive and/or sound isolating material 270 are all shown in FIG. 3B to be oriented at a similar angle, this need not always be the case. For example, second flexible coupling 213B may be oriented at first non-perpendicular angle 215A where second flexible coupling 213B couples to main body housing 211 and speaker wing housing 227 and adhesive and/or sound isolating material 270 may be oriented at a different angle (e.g., parallel to main body housing 211 or at an angle greater or smaller in magnitude than first non-perpendicular angle 215A) where second flexible coupling 213B couples to speaker wing housing 227. First flexible coupling 213A may be flexible and may be oriented at an angle to main body housing 211 in a manner similar to second flexible coupling 213B.

In some embodiments, one or more portions of active auscultation device 203 may be removable from an active auscultation device to, for example, facilitate cleaning and/or electrically charging of one or more components thereof. Additionally, or alternatively, one or more active auscultation device components may be removable to, for example, facilitate downloading and/or uploading of information from/to, for example, memory 240, DSP/controller 230, DSP coefficient controller 240, and/or transceiver 235. Additionally, or alternatively, one or more active auscultation device components may be removable to, for example, facilitate exchange of one component (e.g., a main body housing) for another component (e.g., a replacement main body housing) so that, for example, a first main body housing may be exchanged for a second main body housing when, for example, the components (e.g. power source 245) included in the first main body housing need to be charged, information needs to be downloaded therefrom, and/or a new, or modified, set of instructions is to be uploaded to one or more components of the first main body housing.

An example of an active auscultation device with removable parts 302 is shown in FIGS. 3C-3F in which FIG. 3C provides a top view and FIG. 3D provides a side view of an active auscultation device with removable parts 302 without a main body housing positioned within a cavity 310 formed within a cradle 305. Active auscultation device with removable parts 302 also includes microphone wing housing 222, speaker wing housing 227, first flexible coupling 213A, second flexible coupling 213A. First and/or second flexible coupling(s) 213A and/or 213B of active auscultation device 302 may be oriented at a non-perpendicular angle relative to main body housing in a manner that may be similar that described above with regard to active auscultation device 301.

As may be seen in FIG. 3C, cradle 310 includes a first port 315 and a second port 320 by which a removable main body housing 330 (shown in FIG. 3E) may be electrically, mechanically, and/or communicatively coupled to a removable main body housing 330, a bottom view of which is shown in FIG. 3E. Removable main body housing 330 may house most, or all, of the set of main body components 224 described herein such as and may include a first coupling 316 configured to electrically, mechanically, and/or communicatively couple to first port 315 and a second coupling 321 configured to electrically, mechanically, and/or communicatively couple to second port 320. FIG. 3F provides a side view of active auscultation device with removable parts 302 and shows removable main body housing 330 seated within cradle 305 within cavity 310.

FIG. 3G provides a top view and FIG. 3H provides a side view of another exemplary embodiment of an active auscultation device 303 that includes a first portion of the main body 211A and a second portion of the main body 221B mechanically, electrically, and/or communicatively coupled together via a hinge 320. First portion of the main body 211A may be configured to house a first portion, or subset of set of main body components 224A and a second portion of the main body 221B may be configured to house a second portion, or subset, of the set of main body components 224B. On some occasions, components allocated to the first and second portions of the set of main body components 224A and 224B may include components configured to work with microphone array 222 and speaker array 227, respectively.

Hinge 320 may be configured to allow for articulation of first portion of the main body 211A relative to second portion of the main body 221B in, for example, the Z-direction and may include flexible material that allows for the articulation and/or hinge-like components. Articulation provided by hinge 320 may contribute to an overall flexibility of active auscultation device 303 so that it may be curved to fit a corresponding curvature of a wearer. FIG. 3H shows one example of how second portion of the main body 211B may articulate (in this case upwards as oriented in the figure) relative to first portion of the main body 221A via hinge 320.

FIG. 3H also shows second portion of main body housing 211B oriented at an angle 314A relative to first portion of main body housing 211A so provide one example of how second portion of main body housing 211B may articulate relative to to first portion of main body housing 211A. In addition, FIG. 3H also shows second flexible coupling 213B, speaker wing housing 227, and adhesive and/or sound isolating material 270 oriented at a second non-perpendicular angle 215B relative to the right side (as shown in FIG. 3H) of second portion of main body housing 211B in order to, for example, accommodate a curvature of a wearer so that each component of active auscultation device 303 may be securely physically coupled to and directly abut the wearer's skin.

FIG. 3I provides a top view and FIG. 3J provides a side view of another exemplary embodiment of an active auscultation device 304 that includes a first body 350 and a second body 355 mechanically, electrically, and/or communicatively coupled together via hinge 320. First body 350 may be configured to house a first portion, or subset of set of main body components 224A and microphone wing components 205 and second main body 355 may be configured to house a second portion, or subset, of the set of main body components 224B and speaker wing components 207. On some occasions, components allocated to the first and second portions of the set of main body components 224A and 224B of active auscultation device 303 and 304 may be the same while on other occasions they may differ. FIG. 3J shows one example of how second body 355 may articulate (in this case upwards as oriented in the figure) relative to first body 350 via hinge 320.

Prior to use, any of the active auscultation device(s) (e.g., 203, 301 302, 303 and/or 304) may be positioned at one or more sites (e.g., on skin above/below a left lung, right lung, upper lobe of the lung, lower lobe of the lung, anterior side of the lung, and/or posterior side of the lung) on a wearer's body (e.g., upper/lower chest, upper/lower back, left side and/or right side of the torso, etc.) that may be selected responsively to, for example, the wearer's physiology, gender, disease progression, disease localization, and/or trapped air pocket concentration positions. On some occasions a position and/or orientation of active auscultation device(s) 203, 301 302, 303 and/or 304 on wearer's body may be selected by a medical professional (e.g., pulmonologist, respiratory therapist, etc.) so that an area of interest may be investigated and/or to achieve the most powerful and/or least noisy detected acoustic signals and/or avoid interfering factors (e.g., the diaphragm, adipose tissue, and/or other medical devices). An active auscultation device may be attached to a wearer's body via any acceptable means including, but not limited to, an adhesive, a strap, and/or tape. Active auscultation device 203, 301 302, 303 and/or 304 may be worn for any desired length of time (e.g., 30 minutes-3 weeks).

FIG. 4A is a diagram of an exemplary wearer 400 with an active auscultation device 203, 301, 302, 303, and/or 304 attached to his or her chest below the skin covering the pectoral muscle so that, for example, acoustic energy/waves emanating from the wearers' second lung (as detected by speaker array 230) may be analyzed and, for example, used to generate a model of the wearer's lung and/or air trapped therein as, for example, modeled second lung 105B as shown in FIG. 1C and discussed above, one or more of the spectrographs shown in FIGS. 5A-5D or 6A-6D and/or produce a result via execution of process 800. In some cases, a wearer 400 may wear multiple active auscultation devices that may be positioned at different locations on the wearer's body (e.g., left and right side of the thorax; the wearer's chest and back, etc.).

On some occasions, a medical professional may select a position to place an active auscultation device on wearer's 400 body responsively to a determination of where on the body is likely to produce clear (e.g., as measured by SNR) and/or highly reproducible measurement results. At times, more than one active auscultation device 203, 301 302, 303 and/or 304 may be used to obtain measurements from a variety of different positions, which may facilitate obtaining measurements from a representative portion of the wearer's lung(s), thereby getting an idea of overall lung health and/or disease progression. In one embodiment, an active auscultation device 203, 301 302, 303 and/or 304 may be positioned on wearer's 400 mid-thorax on the right and/or the left side so that conditions within multiple pulmonary lobes and/or lung parenchyma may be measured at the same time, while avoiding a theoretical risk of overrepresenting upper lobe predominant emphysema or lower lobe diaphragmatic interference, thus enabling the interpretation of measurement results as tendencies in the short and long term that are relatively free from overrepresentation of upper lobe predominant emphysema and interference from the diaphragm. In these embodiments, analysis of active auscultation device 203, 301 302, 303 and/or 304 measurements may allow for finding/determining dynamic changes in measurements caused by, for example, exercise, medication effects, and/or early exacerbations of COPD. In some cases, these dynamic changes may be localized, or associated with, for example, a particular position in the wearer's lung or thorax.

FIG. 4B is a diagram of representative components of an exemplary active auscultation device 203, 301 302, 303 and/or 304 in use to measure acoustic energy/waves emanating from an approximation of a lung 425 (represented as an oval) of wearer 400. Lung 425 includes a first, second, and third pocket of trapped air 405A, 405B, and 405C, respectively, wherein air is trapped within the first, second, and third pockets of trapped air 405A, 405B, and 405C even after wearer 400 fully exhales as may the case when the wearer has COPD. FIG. 4B also depicts a pathway for a first emitted acoustic signal 410A, a second emitted acoustic signal 410B, and a third emitted acoustic signal 410C all of which are emitted by a speaker 231 of speaker array 230 toward the lung 425 and/or a first, second, and third pocket of trapped air 405A, 405B, and 405C. FIG. 4B also shows pathways for reflected acoustic signals that are respondent to first emitted acoustic signal 410A, a second emitted acoustic signal 410B, and a third emitted acoustic signal 410C as a first detected acoustic signal 415A (which corresponds to a reflection of first emitted acoustic signal 410A), a second detected acoustic signal 415B (which corresponds to a reflection of second emitted acoustic signal 410B), and a third detected acoustic signal 415C (which corresponds to a reflection of third emitted acoustic signal 410C).

Various techniques may be utilized to distinguish between first emitted acoustic signal 410A, a second emitted acoustic signal 410B, and third emitted acoustic signal 410C from one another upon receipt by microphone 221 so that, for example, characteristics of first, second, and/or third pocket of trapped air 405A, 405B, and/or 405C may be determined via, for example, one or more processes disclosed herein. For example, in some embodiments, first, second, and/or third emitted acoustic signal(s) 410A, 410B, and 410C may be emitted at the same time as part of, for example, a broadband large field emitted acoustic signal. Additionally, or alternatively, first emitted acoustic signal 410A, a second emitted acoustic signal 410B, and third emitted acoustic signal 410C may be emitted at different times (e.g., multiplexing) so first emitted acoustic signal 410A, a second emitted acoustic signal 410B, and third emitted acoustic signal 410C may differentiated from one another using a time of emission/detection. Additionally, or alternatively, first emitted acoustic signal 410A, a second emitted acoustic signal 410B, and third emitted acoustic signal 410C may be directed toward a target region of lung 425 via adjusting an orientation of speaker 221 so that directs first emitted acoustic signal 410A toward first pocket of trapped air 405A, second emitted acoustic signal 410B toward second pocket of trapped air 405B, and third emitted acoustic signal 410C toward third pocket of trapped air 405C. Additionally, or alternatively, first emitted acoustic signal 410A, a second emitted acoustic signal 410B, and third emitted acoustic signal 410C may be emitted from speaker 231 such that each of first emitted acoustic signal 410A, a second emitted acoustic signal 410B, and third emitted acoustic signal 410C has a different frequency and/or has a varying pulse signature. In some embodiments, a characteristic (e.g., frequency and/or intensity) of an emitted acoustic signal may be responsive to a characteristic of a wearer and/or a location of target tissue (e.g., pocket of trapped air and/or a distance between the speaker and/or microphone and the target tissue). For example, second emitted acoustic signal 410B may be emitted with an intensity greater than the intensity for first or third emitted acoustic signal(s) 410A or 410C because the target tissue for second emitted acoustic signal 410B (i.e., second air pocket 405B) is deeper within lung 425 (i.e., further away from speaker 231 and microphone 221) than first or third air pockets 405A or 405C.

Exemplary techniques for distinguishing between the first, second, and third detected acoustic signals 415A, 415B, and 415C include, but are not limited to, frequency analysis (e.g., may be used in embodiments where first, second, and/or third detected acoustic signals 415A, 415B, and 415C contain a different frequency of acoustic signal) and/or time domain analysis (e.g., may be used in embodiments where first, second, and/or third emitted acoustic signals 410A, 410B, and 410C are emitted at different times). Additionally, or alternatively, differences between first, second, and third emitted acoustic signals 410A, 410B, and 410C may be responsive to, for example, a position (e.g., distance away from speaker 231) and/or size of a target trapped air pocket 405A, 405B, and/or 405C. In some embodiments, differences between first, second, and third emitted acoustic signals 410A, 410B, and 410C may be used by, for example, DSP/controller 230 and/or an external processing device to distinguish between the signals, all of which are received by microphone 221. In some cases, first detected signal 415A, second detected signal 415B, and/or third detected signal 415C may be distinguished from one another by, for example, DSP/controller 230 and/or an external processor via, for example, a time they are received (as may occur when each different emitted acoustic signal is projected into the wearer at a different time) and/or a frequency and/or set of frequencies included in the detected signal. Additionally, or alternatively, one or more of the emitted acoustic signals may include a signature (e.g., a set of frequencies or an absence of an acoustic signal) that is embedded in the emitted acoustic signal as it is emitted over time that may be used to distinguish one emitted acoustic signal from another.

It is expected that a distance from an emitter, such as speaker 231 to trapped air positioned within an air pocket like first, second, and third pocket of trapped air 405A,

405B, and 405C back to a receiver like microphone 221 will vary for each trapped air pocket, and that this difference in time may allow for distinguishing between different trapped air pockets via estimating a time delay for each particular stimuli (or frequency of sound).

In some embodiments, emitted acoustic signals may be generated using known frequencies that, in some cases may be and/or may include pseudo-randomly selected sets of frequencies (e.g., a PN sequence). These known frequencies and/or sets of frequencies may make analysis of detected acoustic signals easier by, for example, facilitating a matching of signals from a group, or set of frequencies, aligning detected acoustic signals with one another in, for example, time and/or frequency, for comparison, and/or grouping detected acoustic signals together. The analysis may be performed in order to, for example, detect and/or determine a characteristic (e.g., size, volume, position) of one or more trapped air pockets in a wearer's lung. In some cases, varying the characteristics of the pseudorandom noise included in an emitted acoustic signal may facilitate the fine tuning and/or amplification of portions of the corresponding detected acoustic signal received from different positions and/or from entities within the body, such as trapped air pockets, that may have different resonant cavity size. In some cases, the PN sequence may be represented as and/or correspond to a stream of 1's and 0's (or 1's and −1's) that is derived from a known formula, which outputs binary values that may look and/or behave like random noise but they have a known pattern if initial conditions for their generation are known. To convert the PN sequence into acoustic noise, a known carrier signal (e.g., a sinusoidal wave and/or a series of sinusoidal waves at different frequencies) may be multiplied by the PN sequence, effectively introducing 180 degrees of phase shifts into the carrier signal at random intervals. To a general observer, the original signal looks like noise, but to an observer that knows the PN sequence, and knows the characteristics of the original carrier signal, it may be possible to synchronize detected acoustic signals with one another using a known component and/or compare the detected acoustic signals with the original modified carrier signal to determine one or differences (e.g., loss in some frequencies and/or enhancement in other frequencies) therebetween. The time duration of each 1 and −1 can make the signal better for close or remote air trapped pockets, or make it easier to locate and/or detect air pockets. In some cases, having smaller time durations for 1 and −1 may provide better spatial resolution (in order to, for example, determine a position of a volume of trapped air (i.e., air pocket) because the faster the transitions are, the more bits can be sent to a processor in the same amount of time, which allows for high spatial resolution. Because sound takes some time to travel back and forth through lung or other animal tissue, on some occasions using an emitted acoustic signal that has a higher density of bits that are being transmitted may allow for a more precise match of detected acoustic signals. In order to achieve this spatial resolution, a high sampling frequency may be needed (e.g., above 48 kHz), which is typically beyond hearing range.

Although FIG. 4B shows first, second, and third emitted acoustic signals 410A, 410B, and 410C only being incident on a respective first, second, and third pockets of trapped air 405A, 405B, and 405C this need not always be the case. In some embodiments, one or more of first, second, and/or third emitted acoustic signals 410A, 410B, and 410C may be incident on a plurality of pockets of trapped air 405.

In some embodiments, speaker 231 may emit first, second, and/or third emitted acoustic signals 410A, 410B, and/or 410C at different trajectories and/or with different intensities (power levels) so that they are directed toward different target locations (e.g., trapped air pockets 405A, 405B, and/or 405B) within the wearer. This may serve to focus emitted acoustic signals on one or more trapped air pockets 405A, 405B, and/or 405C. Additionally, or alternatively, frequencies for emitted acoustic signals may be selected that have a likelihood of being resonant with trapped air pockets positioned at different depths of lung tissue (i.e., distance between speaker and air pocket) and, when resonance is found at a frequency associated with a particular depth of tissue and/or position, a corresponding position of a trapped air pocket may be determined. In this way, positions and/or characteristics of various trapped air pockets in a wearer's lung may be plotted or mapped out.

In some embodiments, active auscultation system 203, 301 302, 303 and/or 304 may be configured to use maximum length sequences to feed a single (or multiple) speaker/microphone pairs. Matched filters may then be use to estimate resonance by distance and/or perform multi-resonance simulation. Maximum length sequences may be pseudo-randomly selected sequences of frequencies created using a repeatable generative process, or generative parameters. In some cases, maximum length sequences may have one or more special characteristics wherein their frequency spectrum looks like broadband (or white) noise. At times, two maximum length sequences with different generative parameters might have very similar average frequency spectrums, but filters that match each particular sequence can be created to enable detection of each individual sequence, even in the presence of other signals and/or sequences with different parameters.

FIGS. 5A-5D and 6A-6D respectively provide a first and second sets of exemplary spectrograms of detected acoustic signals that may be generated/detected by a system like system 201 and/or 202 and/or by an active auscultation device like active auscultation device 203, 301 302, 303 and/or 304 when an acoustic signal is projected into a lung. These spectrograms show frequency in Hz on a first Y-axis (on the left as oriented in the figures), magnitude in decibels (dB) on a second Y-axis (on the right as oriented in the figures), and a count of a number of frames×$10^4$ on the X-axis. In some cases, the number of frames may correspond to time (i.e., how many frames have passed by for a corresponding spectrograph measurement). In addition, when the wearer is inhaling and exhaling is also superimposed on the spectrograms along the X-axis. In some cases, the superposition of when the wearer breathes may be manually inserted into the data as it is taken based on, for example, observation of the patient's breathing while the active auscultation device is being used to collect data used to generate the spectrograms. One or more of the spectrograms of 5A-5D and 6A-6D may be used to determine and/or establish a lung signature for the wearer.

More particularly, FIGS. 5A-5D provide spectrograms of a lung with no COPD, wherein FIG. 5A provides a spectrogram 501 in which the instantaneous energy in each frame is represented by the grey-scale bar, or scale, positioned on the right side of the graph, FIG. 5B provides a spectrogram 502 of an energy change, or energy evolution, over time for a control subject without COPD at rest, with a respiratory period of 7 seconds breathing at a rate of 8.57 breaths per minute. In some cases, spectrogram 502 of FIG. 5B may serve as a baseline and changes in energy for other spectrograms for the same, or different, patient(s) may be compared with the baseline of spectrogram 502 and plotted as a difference from the baseline energy. The dynamic range for energy evolution shown in spectrogram 502 of FIG. 5B is on the range of [−8:6] dBs (14 dBs). When the subject increased their respiratory rate to 12 breaths per minute, a smoothed spectrogram 503 is produced as shown in FIG. 5C. FIG. 5D provides a spectrogram 504 that shows an exemplary reduced dynamic range of the energy evolution that is about 7 dBs, with very sharp and localized energy changes.

The first set of exemplary spectrograms 501-504 may be generated/detected by a system like system 201 and/or 202 and/or an active auscultation device like active auscultation device 203, 301 302, 303 and/or 304 when an acoustic signal is projected into a lung with no COPD wherein spectrogram 501 shows a smoothed spectrogram and spectrogram 502 shows an energy evolution for detected acoustic signals before the wearer exercises. Spectrograms 501 and 502 show a relatively large dynamic range of fourteen decibels between the range of [−8:6] dBs that is taken when the wearer is breathing at a relatively slow rate of approximately 8.5 breaths per minute. Spectrogram 503 shows a smoothed spectrogram and spectrogram 504 shows an energy evolution for detected acoustic signals when the wearer from spectrograms 501 and 502 is breathing faster during exercise, which demonstrates a reduced dynamic range when compared with spectrograms 501 and 502, respectively, wherein spectrograms 503 and 504 show dynamic range of seven decibels between the range of [−5:2] dBs that is taken when the wearer is breathing at a relatively faster rate of approximately 12 breaths per minute. In this way, an acoustic signature for a lung during varying respiratory rates of a wearer may be measured and/or established as a baseline of an acoustic signature of a control wearer (i.e., a wearer who is not diagnosed with COPD).

FIGS. 6A, 6B, 6C, and 6D provide a second set of exemplary spectrograms 601, 602, 603, and 604, respectively, of detected acoustic signals that may be generated/detected by a system like system 201 and/or 202 and/or an active auscultation device like active auscultation device 203, 301 302, 303 and/or 304 when an acoustic signal is projected into a lung with severe COPD (i.e., a plurality of trapped air pockets). More particularly, FIG. 6A provides a smoothed spectrogram 601 of a lung when the wearer is breathing about 12 breaths per minute. FIG. 6B is provides a spectrogram 602 shows an energy evolution for detected acoustic signals while the wearer is exercising and/or breathing at a relatively fast rate of twelve breaths per minute and also shows a reduced dynamic range [−4:1] dB in, which energy changes remain very constant across all the spectra. FIG. 6C is provides a spectrogram 603 that shows detected signals when the wearer is exercising when the respiratory rate of the wearer is increased. FIG. 6D provides a spectrogram 604 showing detected signals when the wearer is at rest after the exercise when the respiratory rate of the wearer had decreased to 10 breaths per minute following exercise, but the energy evolution remained with a dynamic range of [−4:1] dBs, or 5 dBs.

Active auscultation measurements taken by, for example, the active auscultation devices described herein may comprise powering the speaker(s) and microphone(s) and transmitting an acoustic signal into a wearer's body toward a region of interest, which often times may be a lung and/or a pocket or volume of trapped air within a lung. The emitted acoustic signal may be, for example, a single frequency, a set of frequencies, a broadband set of frequencies, and/or a white-noise-like broadband set of frequencies. In some instances, the acoustic signal may vary over time. For example, the acoustic signal may be modulated and/or may change frequency over time. The changes in frequency may be random, pseudo-random, and/or sequential (e.g., increasing and/or decreasing at regular intervals (e.g., 10 Hz, 100 Hz, etc.). Additionally, or alternatively, the acoustic energy may have an intensity/power that is sufficient to generate a measurement. In some embodiments, the systems, devices, and methods herein may be configured so that the acoustic signal is not of sufficient intensity/power to by heard by the wearer and/or other individuals in proximity to the wearer.

An acoustic signal resulting from the emitted acoustic signal (i.e., the detected acoustic signal) may be detected by one or more microphones and converted into a digital signal which may be stored on and/or processed by a processor/memory configuration like DSP/controller 230. The detected acoustic signal may be processed by DSP/controller 230 and stored in memory 240.

In some embodiments, the active auscultation devices disclosed herein may be configured to take measurements of varying duration and/or resolution. For example, the measurements may be taken in high, medium, and/or low resolution and the measurements may vary in time.

The high resolution measurements may also be referred to as detailed measurements. In one embodiment, the high-resolution measurements may have, for example, a duration of 3-10 minutes at a data consumption rate of, for example, 203 to 300 kilobytes per minute. Exemplary data storage requirements for a high resolution measurement may be, for example, 1.2 to 1.8 megabytes. In one embodiment, in order to take a high-resolution measurement, the active auscultation device may be required to be connected to an external processing device (e.g., computer system 23, wearer computer device 27, etc.) via a wireless and/or wired communication connection. On some occasions, the external processing device may be running a software application configured to communicate with an active auscultation device like active auscultation devices 203, 301 302, 303 and/or 304 so that, for example, the active auscultation device may communicate measurements when taken in real time thereby bypassing the need to store the measurements in memory 240. Additionally, or alternatively, measurements (e.g., low resolution measurements stored on memory 240 may be communicated to the external processing device upon communicatively coupling to the external processing device. In some embodiments, a high resolution measurement may be triggered by the application, which may also guide the wearer through a series of steps to perform to, for example, initiate a type of measurement being taken, actions the wearer is to take prior to, during, and/or after the measurement is taken (e.g., breathing exercises and/or exercise) Additionally, or alternatively, the software application may ask the wearer one or more questions pertaining to, for example, the wearer's health, the wearer's comfort level/quality of life and/or environmental conditions (e.g., temperature, humidity level, air quality level, etc.). Answers to these questions may be associated with a measurement that is taken by active auscultation device and received by the external computing device. In some instances, the high resolution measurements may be transmitted in real time to the application. In some embodiments, answers to these questions may be scored according to, for example, a scoring formula that may be associated with the questions (as is the case with patient-reported-outcome (PRO) instruments) in order to, for example, quantify the answers and track a patient's answers to the same questions over time.

The low resolution measurements taken by the systems and devices disclosed herein may also be referred to as quick measurements. In one embodiment, the low resolution measurements may have a duration of, for example, 0.5-5 minutes at an exemplary data consumption rate of 28 to 30 kilobytes per minute. An individual low resolution measurement may have a maximum data storage requirement of 40-80 kilobytes. In one embodiment, the active auscultation device may store one or more low resolution measurements in an onboard memory. Stored measurements may be later uploaded to the external processing device upon, for example, synching the active auscultation device with the external communication device. When memory is full, a visual indication on the sensor and application may be displayed, and no new measurements may possible until synchronization with application and memory has been cleared.

In some cases, a noise reduction algorithm (e.g., deterministic beamformer algorithm) may be applied to the detected acoustic signals to, for example, improve a signal-to-noise ratio (SNR). Then, a resulting audio stream may be segmented into frames of, for example, 2-30 ms in duration and a fast Fourier transform (FFT) may be applied to each segment. The segments may then be individually compared to one another and/or a running average of recent segments to find, for example, outliers or noisy segments. The segments may then be analyzed to, for example, estimate the patient's LRS and/or track its variation over time using, for example, 0.5, 10, and 120 second moving averages.

In some embodiments, analysis of the LRS and/or segments may be used to determine, for example, lung volume changes, lung resonance and/or air pocket resonances, breathing capacity, etc. over the patient's respiratory cycle. Additionally, or alternatively, a patient's LRS may be used to derive secondary features such as a main spectral peak (MSP), which is the highest energy level on every spectral frame (see e.g., FIGS. 5A-5D and 6A-6D). Other secondary features may be correlated with the spectral energy evolution (e.g., the difference between fast and slow averages). These features (LRS, lung volume changes, secondary features, etc.) may be used to, for example, track cyclic changes in the LRS of a patient during inhalation and exhalation. From there, respiratory period estimation may be performed so as to, for example, mark respiratory events (inhalations and exhalations) when compared to manual labelling as may be done via visual observation of the patient. FIG. 7 provides a scatter graph 701 comparing labeled respiratory periods for a patient in seconds that are observed as a function of estimated respiratory periods in seconds. The estimated respiratory periods are determined via analysis of 16,000 frames selected from 100 test segments. Scatter graph 701 also provides a linear regression where R2=0.960.

Use of the systems, devices, and methods disclosed herein may be applicable to monitoring many respiratory conditions in addition to COPD and/or air trapping. For example, the active auscultation, and other, measurements obtained by active auscultation device 203, 301 302, 303 and/or 304 may be used to monitor many different lung conditions and/or lung health and/or diagnose one or more lung conditions. For example, measurements obtained by active auscultation device 203, 301 302, 303 and/or 304 may be used to measure and/or diagnose disease and/or disease progression with exemplary lung diseases and/or conditions being inflammation in the bronchial tubes, asthma, pneumonia, cancer, pulmonary embolisms, and/or interstitial lung diseases, which are characterized by a stiffening of the lung tissue. Additionally, or alternatively, the active auscultation, and other, measurements obtained by active auscultation device 203, 301 302, 303 and/or 304 may be used to monitor lung condition over time in order to, for example, assess an effectiveness of treatment (e.g., medication, respiratory therapy, and/or exercise).

FIG. 8 is a flowchart providing the steps of an exemplary process 800 for performing active auscultation using, for example, the active auscultation device disclosed herein. Process 800 may be executed by one or more of the systems and/or system components disclosed herein such as system(s) 201 and/or 202 and/or an active auscultation devices like active auscultation device 203, 301, 302, 303.

Optionally, in step 805, an indication of an activation and/or trigger to begin projecting an acoustic signal like emitted acoustic signals 405A, 405B, and/or 405C acoustic signal(s) into a wearer's thorax may be received by, for example, a processor of an active auscultation device such as DSP/controller 230. The activation and/or trigger may be, for example, an indication from an inertial motion unit such as IMU 250 that a wearer has moved (e.g., inhaled, exhaled, began walking, etc.) and/or may be responsive to an instruction stored in a memory, such as memory 240, that, for example, a scheduled and/or periodic active auscultation measurement is to be taken by active auscultation device.

In step 810, an acoustic signal and/or a set of acoustic signals may be projected into the wearer's thorax toward the wearer's lungs (e.g., lung 425) by one or more speakers such as speaker 231 of speaker array 230 as shown in, for example, FIG. 4B. In some embodiments, execution of step 810 may be responsive to execution of step 805. Then, in step 815, one or more detected acoustic signals that have passed through the and/or reflected from the wearer's tissue (e.g., lung tissue) may be detected by one or more microphones such as microphone 220 and communicated to/received by a processor such as DSP/controller 230 and/or processor 204. Optionally, in step 820, the received detected acoustic signal may then be pre-processed to, for example, remove noise, filter out frequencies of sound that are undesirable (e.g., application of a bandpass filter), and/or compress the data making up the detected acoustic signal. Additionally, or alternatively, in step 820 the detected acoustic signal may be sampled at, for example, a periodic interval (e.g., a 0.5 s sample every 3 seconds or a 1 s sample every five seconds).

Optionally, in step 825, it may be determined whether the signal quality of the detected acoustic signal is below a threshold value (e.g., signal-to-noise ratio (SNR)) and/or whether movement of an active auscultation device using used to execute process 800 and/or provide information that may be received during execution of process 800 has been detected. When determining if the signal quality is below a threshold value, step 825 may be executed by, for example, an onboard processor like DSP/controller 230 and/or an external processor 204. When step 825 is performed by an external processor, execution of step 825 may include analysis of the received signal to determine if it is being wirelessly transmitted correctly and/or without interference from, for example, the body (e.g., water content) of the wearer. When the signal quality is below the threshold, a calibration sequence may be performed (step 830). One some occasions, performing the calibration sequence may include transmitting the acoustic signal from one or more speakers of a speaker array like speaker array 230 and/or analysis of detected acoustic signals received by one or more microphones of a microphone array like microphone array 220 to determine one or more speaker/microphone pair(s) that provide, for example, the clearest detected acoustic signal and/or a detected acoustic signal that is above the threshold SNR.

When execution of step 825 indicates no movement has been detected, process 800 may proceed to step 835. When movement is detected via, for example, IMU 250, visual observation of a clinician, and/or via a device communicatively coupled to the active auscultation device (e.g., a device triangulating a position of the active auscultation device such as computer system 23 and/or wearer computer device 27) a calibration process may be performed to, for example, optimize operation of microphone(s) and/or speakers(s) used by the active auscultation device to capture the detected acoustic signal and thereby optimize one or more features (e.g., SNR, intensity, power, etc.) of the detected acoustic signal.

In step 835, the detected acoustic signal, sampled detected acoustic signal, and/or pre-processed detected acoustic signal may be analyzed to determine one or more characteristics thereof and a result of the analysis may be used to, for example, determine a lung signature for the wearer, a volume of trapped air within the wearer's lung(s), a degree of respiratory function for the wearer, and/or an indication of respiratory health for the wearer (step 840). In step 845, a result of the analysis of step 835 (e.g., a spectrograph), and/or an indication of the wearer's lung resonance signature may be provided to a display device like display 209.

I claim:
1. A device for performing active auscultation comprising:
   a speaker wing housing that houses a speaker configured to project an acoustic signal into a patient's skin responsively to an electrical signal received from a controller;
   a microphone wing housing that houses a microphone configured to detect a detected acoustic signal emanating from the patient's skin and communicate the detected acoustic signal to the controller; and
   a main body housing physically and communicatively coupled to the microphone wing housing via a first coupling and physically and mechanically coupled to the speaker wing housing via a second coupling, the main body housing comprising:
      a transceiver communicatively coupled to the controller and a memory, the transceiver being configured to communicate the detected acoustic signal to an external device and receive instructions from the external device;
      the memory communicatively coupled to the controller and the transceiver, the memory being configured to receive instructions from the transceiver and store a set of instructions for execution by the controller;
      the controller configured to generate an electrical signal responsively to an instruction stored in the memory and communicate the electrical signal to the speaker, receive the detected acoustic signal from the microphone and communicate the detected acoustic signal to the transceiver; and
      a battery electrically coupled to the speaker, the microphone, the transceiver, the memory, and the controller, the battery being configured to provide electrical power to the speaker, the microphone, the transceiver, the memory, and the controller.
2. The device for performing active auscultation of claim 1, wherein the controller is further configured to pre-process the detected acoustic signal to remove noise.
3. The device for performing active auscultation of claim 1, wherein the speaker wing housing houses an array of a plurality of speakers.

4. The device for performing active auscultation of claim 1, wherein one or both of the microphone wing housing houses an array of a plurality of microphones and/or the speaker wing housing houses an array of a plurality of speakers.

5. The device for performing active auscultation of claim 1, wherein the main body housing includes a first section that is physically coupled to a second section via a flexible hinge.

6. The device for performing active auscultation of claim 1, wherein a surface of at least one of the microphone wing housing, speaker wing housing, and main body housing is configured to be acoustically coupled to the patient's skin via at least one of an elastic band, a sleeve, a garment, and an adhesive.

7. The device for performing active auscultation of claim 1, wherein the at least one of the first coupling and the second coupling is flexible and device is configured to curve via the flexibility of the at least one of the first coupling and the second coupling.

8. The device for performing active auscultation of claim 1, wherein the memory is further configured to store the detected acoustic signal.

9. The device for performing active auscultation of claim 1, further comprising:

a motion detector for detecting a movement of the device.

10. The device of claim 9, wherein the controller is further configured to perform a calibration of the speaker and the microphone responsively to receipt of a detected movement from the motion detector.

11. A method for performing active auscultation comprising:

receiving, by a processor, a first detected acoustic signal, the first detected acoustic signal corresponding to a first incident acoustic signal projected into the thorax of a wearer of an active auscultation device;

receiving, by the processor, an indication that the wearer's body has moved;

initiating, by the processor, performance of a calibration sequence for the active auscultation device responsively to receipt of the indication that the wearer has moved;

receiving, by the processor, a second detected acoustic signal, the second detected acoustic signal corresponding to a second incident acoustic signal projected into the thorax of the wearer of the active auscultation device, the second detected acoustic signal and the second incident acoustic signal being different from the respective first detected acoustic signal and the first incident acoustic signal due to performance of the calibration sequence;

analyzing, by the processor, the first and second detected acoustic signals;

determining, by the processor, a characteristic of a wearer's lung using the analysis; and providing, by the processor, an indication of the characteristic to a user.

12. The method of claim 11, further comprising:

receiving, by the processor, a previously determined characteristic of the wearer's lung;

comparing, by the processor, the characteristic of the wearer's lung and the previously determined characteristic of the wearer's lung; and providing, by the processor, an indication of the comparison to the user.

13. The method of claim 11, wherein the characteristic of the wearer's lung is an acoustic lung signature.

14. The method of claim 11, wherein the characteristic of the wearer's lung is a volume of air trapped in the wearer's lung.

15. The method of claim 11, wherein the characteristic of the wearer's lung is a number of pockets of trapped air present in the wearer's lung.

16. The method of claim 11, wherein the characteristic of the wearer's lung is a size of one or more pockets of trapped air present in the wearer's lung.

17. The method of claim 11, wherein the characteristic of the wearer's lung is a position of one or more pockets of trapped air present in the wearer's lung.

18. The method of claim 12, wherein previously determined characteristic of the wearer's lung is a first acoustic lung signature and the characteristic of the wearer's lung is a second acoustic lung signature.

19. The method of claim 12, wherein the previously determined characteristic of the wearer's lung is a first volume of air trapped in the wearer's lung and the characteristic of the wearer's lung is second volume of air trapped in the wearer's lung.

20. The method of claim 12, wherein the previously determined characteristic of the wearer's lung is a first number of pockets of trapped air present in the wearer's lung and the characteristic of the wearer's lung is a second number of pockets of trapped air present in the wearer's lung.

21. The method of claim 12, wherein the previously determined characteristic of the wearer's lung is a first size of one or more pockets of trapped air present in the wearer's lung and the characteristic of the wearer's lung is a second size of one or more pockets of trapped air present in the wearer's lung.

22. The method of claim 12, wherein the previously determined characteristic of the wearer's lung is a first position of one or more pockets of trapped air present in the wearer's lung and the characteristic of the wearer's lung is a position of one or more pockets of trapped air present in the wearer's lung.

* * * * *